(12) United States Patent
Inoue et al.

(10) Patent No.: US 6,291,671 B1
(45) Date of Patent: Sep. 18, 2001

(54) PROCESS FOR PRODUCING DRUG COMPLEXES

(75) Inventors: Kazuhiro Inoue; Hiroshi Susaki; Masahiro Ikeda, all of Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/147,341

(22) PCT Filed: Jun. 5, 1997

(86) PCT No.: PCT/JP97/01915

§ 371 Date: Mar. 22, 1999

§ 102(e) Date: Mar. 22, 1999

(87) PCT Pub. No.: WO97/46261

PCT Pub. Date: Dec. 11, 1997

(30) Foreign Application Priority Data

Jun. 6, 1996 (JP) .................................................... 8-144522

(51) Int. Cl.⁷ ........................... C08B 37/02; C08B 37/08; C07H 13/02; C07K 5/00
(52) U.S. Cl. ........................... 536/123.1; 536/20; 536/21; 536/112; 536/115; 536/119; 536/123.12; 530/300; 530/322
(58) Field of Search .................................... 530/300, 322; 536/20, 21, 112, 115, 119, 123.1, 123.12

(56) References Cited

U.S. PATENT DOCUMENTS

| | | | |
|---|---|---|---|
| 5,688,931 | * 11/1997 | Nogusa et al. | 536/20 |
| 5,837,673 | 11/1998 | Tsujihara et al. | |

FOREIGN PATENT DOCUMENTS

| | | |
|---|---|---|
| 0059221 | 9/1982 | (EP) . |
| 497524 | * 5/1992 | (EP) . |
| 0640622 | 3/1995 | (EP) . |
| 0757049 | 2/1997 | (EP) . |
| 59-220197 | 12/1984 | (JP) . |
| 5-39306 | 2/1993 | (JP) . |
| 6-87746 | 3/1994 | (JP) . |
| 7-84481 | 9/1995 | (JP) . |
| 92/14759 | 9/1992 | (WO) . |
| 94/19376 | 9/1994 | (WO) . |
| 97/46260 | 12/1997 | (WO) . |
| 98/427721 | * 10/1998 | (WO) . |

OTHER PUBLICATIONS

Fujita et al. J.. Pharmacol. and Exper. Therap., 263, 971–978, Mar. 1992.*

Abstracts of 10th Meeting of the Japan Society of Drug Delivery System, 279, 1994.

Abstracts of 9th Annual Meeting of Japanese Society for the Study of Xenobiotics, S 292, 1994, Xenobiotic Metabolism and Disposition, vol. 9 Supplement 1994.

Abstracts of 19th Seminar of Trends in Research and Development, pp. D–9 to D–12, 1995 1994.

Abstracts of 12th Colloid and Interface Technology Symposium, The Chemical Society of Japan, pp. 51–58, 1995 1994.

English Language abstract of JP–5–39306.

English Language abstract of JP–59–220197.

English Language Abstract of WO 92/14759.

Database WPI, Derwent Publication, XP 002149722, an abstract of JP 57–046920.

English translation of Abstracts of 10th Meeting of the Japan Society of Drug Delivery System in 1994, No. 279.

English translation of Abstracts of 9th Annual Meeting of Japanese Society for the Study of Xenobiotics, Xenobiotic Metabolism and Disposition, vol. 9 Supplement (1994).

English translation of Abstracts of 19th Seminar of Trends in Research and Development, pp. D–9 to D–12, held on Feb. 16, 1995.

English translation of Abstracts of 12th colloid and Interface Technology Symposium, The Chemical Society of Japan, pp. 51–58 (1995).

* cited by examiner

Primary Examiner—Michael Borin
(74) Attorney, Agent, or Firm—Greenblum & Bernstein, P.L.C.

(57) ABSTRACT

A method for preparing a drug complex in which a polysaccharide derivative having carboxyl groups and a residue of a drug compound are bound to each other by means of a spacer comprising an amino acid or a spacer comprising peptide-bonded 2 to 8 amino acids, or a drug complex in which a polysaccharide derivative having carboxyl groups and a residue of a drug compound are bound to each other without the spacer, characterized in that an organic amine salt of the polysaccharide derivative having carboxyl groups is reacted with the drug compound or the spacer bound to the drug compound in a non-aqueous system. The reaction between the polysaccharide derivative having carboxyl groups and the drug compound bound with the spacer or the like can be carried out in high yields, and when a drug compound having a lactone ring is subjected to the reaction, side reactions can be reduced.

13 Claims, 11 Drawing Sheets

PROCESS FOR PRODUCING DRUG COMPLEXES

BACKGROUND OF THE INVENTION

1. Field of the Invention

The present invention relates to a method for preparing a drug complex in which a polysaccharide derivative and a drug compound such as antineoplastic agents are bound to each other.

2. Discussion of Background Information

Antineoplastic agents, used for treatment of solid cancers such as lung cancer or digestive organ carcinomas and blood cancers such as leukemia, are systemically administered through routes of administration such as intravenous or oral administration, and then, are distributed to specific tumorous sites and inhibit or suppress the proliferation of cancer cells to exhibit their therapeutic efficacy. However, the systemically-administered antineoplastic agents are rapidly taken into livers and reticuloendothelial organs from blood, or rapidly excreted into urine, and accordingly, their blood concentrations may sometimes be lowered to allow the distribution into tumorous sites to be insufficient. In addition, common antineoplastic agents themselves have poor distribution-selectivity to tumorous sites (tumor selectivity), and therefore, the antineoplastic agents are uniformly distributed over various tissues and cells of the whole body and act as cytotoxins also against normal cells and tissues, which results in problems of the appearance of adverse effects, e.g., emesis, pyrexia, or alopecia at an extremely high rate. Therefore, it has been desired to develop a means of efficiently and selectively distributing antineoplastic agents to tumorous sites.

As one of such means, a process was proposed in which a polysaccharide derivative having carboxyl groups is used as a drug delivery carrier, and an antineoplastic agent is bound to the polysaccharide derivative to delay the disappearance of the antineoplastic agent from blood and to enhance selectivity to tumor tissues. For example, International Publication WO94/19376 discloses a drug complex in which a peptide chain (the number of amino acid residues: 1 to 8) is bound to a carboxyl group of a polysaccharide having carboxyl groups, and doxorubicin, daunorubicin, mitomycin C, bleomycin or the like is further bound by means of the peptide chain. In addition, Japanese Patent Publication (KOKOKU) No. (Hei) 7-84481/1995 discloses a drug complex in which the aforementioned antineoplastic agent is introduced into a carboxymethylated mannoglucan derivative by means of a Schiff base or an acid amide bond. These drug complexes are characterized in that they have more excellent antitumor activity compared to the antitumor agent, per se, that is not bound to a drug delivery carrier, and reduced toxicity and adverse effects.

As for technologies relating to drug complexes utilizing polyalcoholized polysaccharide derivatives as drug delivery carriers, some reports are available, for example, "Researches on polysaccharide-peptide-doxorubicin complexes-Correlations between stabilities of polysaccharide carriers in blood and their anti-neoplastic activities" (Abstracts of 10th Meeting of the Japan Society of Drug Delivery System, 279, 1994); "Researches on polysaccharide-peptide-doxorubicin complexes— Pharmacokinetics and anti-neoplastic activity" (Abstracts of 9th Annual Meeting of Japanese Society for the study of xenobiotics, 292, 1994); Abstracts of 19th Seminar of Trends in Research and Development (held by *The Organization for Drug A D R Relief. R&D Promotion and Product Review*), D-9, 1995; and "Researches on drug delivery to a tumor tissue by polysaccharide carriers" (Abstracts of 12th Colloid and Interface Technology Symposium, The Chemical Society of Japan, 51, 1995).

These drug complexes have conventionally been manufactured by preparing sodium salt of a polysaccharide derivative having carboxyl groups, e.g., carboxymethylpullulan or carboxymethylmannoglucan, and then binding a carboxyl group of the polysaccharide derivative to an amino group of an antitumor agent (or a N-terminal amino group of a peptide chain binding to the antitumor agent) by means of an acid-amide bond. Sodium salt of polysaccharide derivatives is totally insoluble in organic solvents in the least, and accordingly, when carrying out the above reaction, the process has been adopted which comprises preparing sodium salt of a polysaccharide derivative as a solution in water or an aqueous organic solvent containing water, and then dissolving a condensing agent and an antitumor agent (or an antitumor agent having a peptide chain) in the form of hydrochloride or the like in the solution.

However, in the reaction, dehydration condensation is performed in a solvent containing water, and accordingly, it was impossible to obtain a desired product in high yields. Antitumor agents used as reaction materials are generally expensive, and it has been desired to develop a method for efficiently producing the aforementioned drug complexes from a viewpoint of the manufacturing cost. In addition, the compounds described in the Japanese Patent tjnexamined Publication (KOKAI) No. (Hei) 6-87746/1994, which are useful as antitumor agents, have a lactone ring in their molecules, and there are problems that, when these compounds each bound to a peptide chain are subjected to the aforementioned reaction, the lactone ring is opened in the presence of a base and water, and the resulting carboxyl group may react with the N-terminal amino group of the peptide chain bound to the antitumor agent to significantly reduce the yield of the desired product and fail to give the desired uniform drug complex. Therefore, it has been desired to develop a reaction method which can avoid the generation of compounds whose lactone ring is opened.

SUMMARY OF THE INVENTION

The present invention is to provide a method for efficiently producing drug complexes which are capable of site-selectively delivering an active ingredient such as antitumor agents or anti-inflammatory agents to tumorous sites or the like. More specifically, the present invention is to provides a method capable of producing the drug complexes in a large scale and at low cost by efficiently reacting a polysaccharide derivative having carboxyl groups with a drug compound such as antitumor agents or with a spacer comprising an oligopeptide or the like that is bound to a drug compound.

The present inventors conducted intensive researches, and a result, they found that, when a polysaccharide derivative having carboxyl groups is reacted with a drug compound or a spacer bound to a drug compound by using organic amine salt of the polysaccharide derivative instead of the sodium salt used conventionally, the salt of the polysaccharide derivative can be dissolved at a high concentration in an organic solvent substantially free from water so that the reaction of the polysaccharide derivatives with the drug compound or the spacer bound to the drug compound can be performed in extremely high yields, and that by-products or the like can be reduced. The present invention was achieved on the basis of these findings.

The present invention thus provides a method for preparing a drug complex in which a polysaccharide derivative having carboxyl groups and a residue of a drug compound are bound to each other by means of a spacer comprising an amino acid or a spacer comprising peptide-bonded 2 to 8 amino acids, or a drug complex in which a polysaccharide derivative having carboxyl groups and a residue of a drug compound are bound to each other without the spacer, characterized in that an organic amine salt of the polysaccharide derivative having carboxyl groups is reacted with the drug compound or the drug compound bound to the spacer in a non-aqueous system; and a method for preparing the aforementioned drug complex, which comprises the steps of (1) converting an alkali metal salt of the polysaccharide derivative having carboxyl groups into an organic amine salt thereof, and (2) reacting the organic amine salt with the drug compound or the drug compound bound to the spacer in a non-aqueous system.

According to preferred embodiments of the present invention, there are provided the above method wherein the polysaccharide derivative having carboxyl groups is a carboxy($C_{1-4}$)alkyldextran polyalcohol; the above method wherein the dextran polyalcohol that constitutes the carboxy ($C_{1-4}$)alkyldextran polyalcohol is a dextran polyalcohol obtained by treating a dextran under conditions that enable substantially complete polyalcoholization; the above method wherein the carboxy($C_{1-4}$) alkyldextran polyalcohol is a carboxymethyldextran polyalcohol; the above method wherein the carboxy($C_{1-4}$)alkyldextran polyalcohol is a carboxymethyldextran polyalcohol having a molecular weight in the range of from 5,000 to 500,000, preferably in the range of from 50,000 to 450,000, and more preferably in the range of from 200,000 to 400,000, and the degree of carboxymethylation per constitutive saccharide residue is in the range of from 0.01 to 2.0, preferably in the range of from 0.1 to 1.0, and more preferably in the range of from 0.3 to 0.5; and the above method wherein the drug compound is an antineoplastic agent or an anti-inflammatory agent.

According to further preferred embodiments of the present invention, there are provided the above method wherein the drug compound is a compound which can form a lactone ring; the above method wherein a drug compound in which a lactone ring is formed or a spacer bound to a drug compound in which a lactone ring is formed is used for the reaction of the organic amine salt with the drug compound or the spacer bound to the drug compound; and the above method wherein the drug compound which can form a lactone ring is (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione.

DETAILED DESCRIPTION OF THE PRESENT INVENTION

Figure 1:
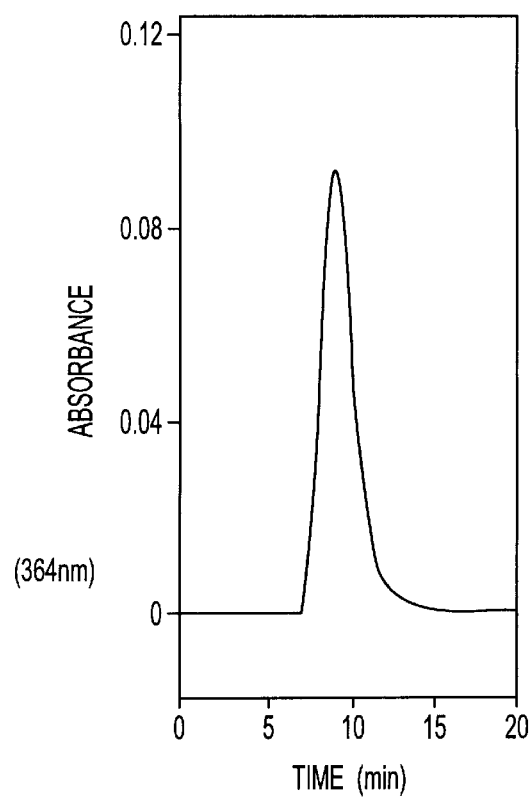
FIG. 1 shows the GPC chart of the drug complex of Example 8 prepared by the method of the present invention.

The drug complex prepared by the method according to the present invention is characterized in that a polysaccharide derivative having carboxyl groups and a residue of a drug compound are bound to each other by means of a spacer comprising an amino acid or a spacer comprising peptide-bonded 2 to 8 amino acids, or a polysaccharide derivative having carboxyl groups and a residue of a drug compound are bound to each other without the spacer. The residue of a drug compound contained in the drug complex is derived from a drug compound used for therapeutic and/or preventive treatment of diseases of mammals including humans as a medicament, for example, an antineoplastic agent, an anti-inflammatory agent, an antibacterial agent or the like, and the residue is composed of a partial structure of the drug compound. However, the drug compound which the residue is derived from is not limited to those mentioned above. In addition, as the drug compound, any compounds may be used so long as they have one or more reactive functional groups capable of participating in bond formation with a polysaccharide derivative or a spacer (for example, amino group, carboxyl group, hydroxyl group, thiol group, ester group or the like). The term "drug compound" in the present specification also includes a prodrug compound which contains, as a part thereof, a major structure of a drug compound having pharmacological activity, per, se, and can reproduce the compound in vivo.

More specifically, the term "residue of drug compound" in the present specification means a partial structure derived from the drug compound existing in the compound after bond formation, assuming that a bond between the polysaccharide derivative or the spacer and the residue of a drug compound is formed through a reaction of a reactive functional group of the drug compound and a reactive functional group of the polysaccharide derivative or the spacer (e.g., dehydration condensation etc.). For example, when the drug compound is represented by D—NH$_2$, D—COOH, D—COOR, D—OH, D—SH, D—CONH$_2$, or D—NH—COOR (R is a lower alkyl group or the like), the residue of the drug compound is represented by D—NH—(D—NH—CO—Q etc.), D—CO—(D—CO—NH—Q, D—CO—O—Q, D—CO—S—Q, etc.), D—CO— (D—CO—NH—Q, D—CO—O—Q, D—CO—S—Q, etc.), D—O— (D—O—CO—Q, D—O—Q, etc.), D—S— (D—S—CO—Q, D—S—Q, etc.), D—CONH— (D—CO—NH—CO—Q etc.), and D—NH—CO— (D—NH—CO—O—Q, D—NH—CO—NH—Q, etc.), respectively (the parenthesized represents a bond between the spacer or the polysaccharide derivative and the residue of the drug compound, wherein Q represents a remaining partial structure of the spacer and the polysaccharide derivative excluding a reactive functional group and a carboxyl group, respectively). However, the sort of the bond between the spacer or the polysaccharide derivative and the residue of the drug compound is not limited to those mentioned above. The residue of the drug compound may be bound to a carboxyl group of the polysaccharide derivative, the N-terminal amino group or the C-terminal carboxyl group of the spacer, or a reactive functional group existing in an amino acid that constitutes the spacer.

As the residue of the drug compound, for example, residues of antineoplastic agents such as doxorubicin, daunorubicin, mitomycin C, bleomycin, cyclocytidine, vincristine, vinblastine, methotrexate, platinum antineoplastic agents (cisplatin or derivatives thereof), taxol or derivatives thereof, camptothecin or derivatives thereof (antitneoplastic agents described in Japanese Patent Unexamined Publication (KOKAI) No. (Hei) 6-87746/1994, preferably (1S,9S)-1-amino-9-ethyl-5-fluoro-2,3-dihydro-9-hydroxy-4-methyl-1H, 12H-benzo[de]pyrano[3',4':6,7] indolizino[1,2-b]quinoline-10,13-(9H,15H)-dione disclosed in claim 2, or the like) may preferably be used. In addition, residues of steroidal anti-inflammatory agents such as hydrocortisone succinate and prednisolone succinate and nonsteroidal anti-inflammatory agents such as mefenamic acid, flufenamic acid, diclofenac, ibuprofen, and tinoridine are also preferred.

The residue of the drug compound may directly bind to the polysaccharide, or may bind by means of a spacer. As the spacer, those comprising one amino acid or peptide-bonded 2 to 8 amino acids may be used. More specifically, where the residue of the drug compound and the polysaccharide derivative are bound to each other by means of a spacer, the spacer has a form of a residue of one amino acid, which means a residue obtained by removing one hydrogen atom and one hydroxyl group from an amino group and a carboxyl group of the amino acid, respectively, or a residue of an oligopeptide comprising peptide-bonded 2 to 8 amino acids, which means a residue obtained by removing one hydrogen atom and one hydroxyl group from the N-terminal amino group and the C-terminal carboxyl group of the oligopeptide, respectively.

Preferred spacers are residues of oligopeptides comprising 2 to 6 amino acids. The sort of the amino acid constituting of the spacer is not particularly limited, and for example, L- or D-amino acids, preferably L- amino acids can be used, and β-alanine, ε-aminocaproic acid, γ-aminobutyric acid or the like may also be used as well as α-amino acids. These amino acids other than α-amino acids are preferably located close to the polysaccharide derivative in the spacer.

For example, where an oligopeptide spacer is used, the bonding direction is not particularly limited, and generally, the N-terminus of the spacer can be bound to a carboxyl group of the carboxy($C_{1-4}$)alkyldextran polyalcohol by means of an acid-amide bond, and the C-terminus of the spacer can be bound to an amino group of the drug compound. Alternatively, for example, where a lysine residue is incorporated as a constitutional unit of the peptide spacer, the α-amino group and the ε-amino group of the lysine residue are allowed to form respective acid-amide bonds with carboxyl groups of other amino acids so as to form N-terminuses at both ends of the peptide spacer, which enable bond formation with carboxyl groups of the drug compounds. Moreover, by incorporating one or more residues of diamine compounds or dicarboxylic acid compounds (residues of diamine compounds such as ethylenediamine or dicarboxylic acid compounds such as succinic acid) in a spacer as constitutional units, a spacer having either N-terminuses or C-terminuses at both ends may be utilized.

Where a spacer comprising an oligopeptide is used, the amino acid sequence is not particularly limited. Preferably used spacers include, for example, a spacer being a residue of a dipeptide represented by —X—Z—, wherein X represents a residue of a hydrophobic amino acid and Z represents a residue of a hydrophilic amino acid; and X—Z— means a residue which consists of a dipeptide that is formed by a peptide bond between a hydrophobic amino acid (X) and a hydrophilic amino acid (Z) at the N-terminal side and the C-terminal side, respectively, and whose one hydrogen atom and one hydroxyl group are removed from the amino group at the N-terminus and the carboxyl group at the C-terminus, respectively, and a spacer containing a residue of the dipeptide as a partial peptide sequence. As the hydrophobic amino acid, for example, phenylalanine, tyrosine, leucine or the like can be used, and as the hydrophilic amino acid, for example, glycine, alanine or the like can be used. The spacer may have a repeated sequence of the dipeptide residue (for example, X—Z—X—Z—, —X—Z—X—Z—X—Z—, etc.).

By using the spacer containing such dipeptide structure, the spacer can be hydrolyzed in tumorous sites or inflammatory sites, which is considered abundant in peptidase to release the drug compound at high concentration in the sites, and accordingly, the structure formed between the spacer containing the above dipeptide and the drug compound by binding to each other is a preferred partial structure of the drug complex according to the method of the present invention. Where a residue of an antineoplastic agent exhibiting concentration-dependent antineoplastic activity (antineoplastic agents exhibiting more potent antineoplastic activity at higher concentration: concentration-dependent antineoplastic agents, e.g., doxorubicin etc.) is used as the residue of the drug compound, a spacer composed of the above dipeptide residue represented by —X—Z— or a spacer containing the above dipeptide residue as a partial peptide sequence may most preferred be used.

In addition, where a time-dependent type antineoplastic agent which requires a retained working time at over certain concentration is used as the residue of the drug compound, enhanced antineoplastic activity may sometimes be obtained by using the above spacer. Examples include the antineoplastic agents disclosed in the Japanese Patent Unexamined Publication (KOKAI) No. (Hei) 6-87746/1994, preferably the antineoplastic agent disclosed in claim 2. Generally, the spacer should not be limited to those mentioned above, and it is necessary to choose an appropriate spacer from viewpoints of the mode of action of the antineoplastic agent, characteristics in pharmacokinetics or appearance of toxicity, releasability in vivo of the antineoplastic agent and the like. For carcinomas exhibiting rapid proliferation, it is generally preferred to choose the above spacer capable of releasing the drug compound at high concentration in a short time.

Specific examples of the spacer are shown in the following table; however, the spacer used for the method for preparing the drug complexes of the present invention is not limited to those mentioned below, and it can be readily understood that one of ordinary skilled in the art can appropriately choose a spacer so as to achieve an optimum releasing rate of a drug compound. In the table, the left ends of peptide sequences are N-terminuses and the residues of drug compounds are bound to C-terminuses. D-Phe represents a D-phenylalanine residue and the other amino acids represent L-amino acids. The degrees of the releasing rate were judged from the degree of appearance of efficacy of the drug complexes bound with doxorubicin against Walker 256 tumor-bearing rats, or from the free doxorubicin concentration at tumorous sites of Walker 256 tumor-bearing rats. Among these spacers, a spacer which can release the drug compound at high concentration in a short time, e.g., (N-term inus)-Gly-Gly-Phe-Gly-, is preferably used for doxorubicin.

TABLE 1

(a) Spacers having high releasing rate

-Leu-Gly-
-Tyr-Gly-
-Phe-Gly-
-Gly-Phe-Gly-
-Gly-Gly-Phe-Gly-
-Gly-Phe-Gly-Gly-
-Phe-Gly-Gly-Gly-
-Phe-Phe-Gly-Gly-
-Gly-Gly-Gly-Phe-Gly- (b) Spacers having relatively high releasing rate -Gly-Gly-Phe-Phe-
-Gly-Gly-Gly-Gly-Gly-Gly- (c) Spacers having relatively low releasing rate -Phe-Phe-
-Ala-Gly-
-Pro-Gly-
-Gly-Gly-Gly-Phe- (d) Spacers having low releasing rate -Gly-
-D-Phe-Gly-
-Gly-Phe-
-Ser-Gly-
-Gly-Gly- TABLE 1-continued -Gly-Gly-Gly-
-Gly-Gly-Gly-Gly- As the polysaccharide derivative having carboxyl groups that constitutes the polysaccharide-derivative moiety of the drug complex, for example, any polysaccharide and chemically or biologically modified derivatives thereof may be used so long as they have carboxyl groups in their molecules. For example, polysaccharides such as hyaluronic acid, pectic acid, alginic acid, chondroitin, and heparin; and polysaccharides such as pullulan, dextran, mannan, chitin, inulin, levan, xylan, araban, mannoglucan, and chitosan in which all or a part of hydroxyl groups are introduced with functional groups having a carboxyl group can be used. For example, those having carboxy($C_{1-4}$)alkylated hydroxyl groups or those having hydroxyl groups esterified with one of carboxyl groups of a polybasic acid can preferably be used. In addition, those obtained by polyalcoholizing the above polysaccharides and then introducing functional groups having a carboxyl group may also be used.

Among those polysaccharide derivatives, a carboxy ($C_{1-4}$)alkyldextran polyalcohol is preferred. Although the degree of polyalcoholization of the carboxy ($C_{1-4}$) alkyldextran polyalcohol is not particularly limited, it is preferred that the dextran polyalcohol constituting the carboxy($C_{1-4}$)alkyldextran polyalcohol is a dextran polyalcohol obtained by treating a dextran under a condition which enables substantially complete polyalcoholization.

The sort of the dextran used for the preparation of the carboxy($C_{1-4}$)alkyldextran polyalcohol is not particularly limited, and the dextran may contain α-D-1,6-bonds at any rate. For example, dextrans containing α-D-1,6-bond at the rate of 85% or more, 90% or more, and 95% or more can be used. The molecular weight of the dextran is not particularly limited, and for example, dextrans having a molecular weight of from about 10,000 to about 2,000,000, preferably from about 50,000 to about 800,000 can be used. As the $C_{1-4}$ alkyl group constituting the carboxy($C_{1-4}$)alkyl group of the carboxy($C_{1-4}$)alkyldextran polyalcohol, a linear or branched $C_{1-4}$alkyl group, specifically, methyl group, ethyl group, n-propyl group, isopropyl group, n-butyl group, sec-butyl group or the like can be used, and methyl group can preferably be used.

The method of the present invention is characterized in that, for preparing the aforementioned drug complex, an organic amine salt of the polysaccharide derivative having carboxyl groups is reacted with the drug compound, per se, or an organic amine salt of the polysaccharide derivative having carboxyl groups is reacted with a spacer bound to the drug compound in an organic solvent substantially free from water, i.e., a non-aqueous system. As a preferred embodiment of the method of the present invention, a method using a carboxy($C_{1-4}$)alkyldextran polyalcohol as the polysaccharide derivative will be specifically explained below. However, the scope of the present invention is not limited to the embodiment.

When a dextran is used as a starting material, the dextran can be treated successively with a large excess amount of sodium periodate and sodium borohydride to obtain a dextran polyalcohol subjected to substantially complete polyalcoholization. However, the method for the polyalcoholization of dextrans is not limited to the method mentioned above, and any method available to those skilled in the art may be adopted. The carboxy($C_{1-4}$)alkylation can be carried out, for example, by reacting a halogenated $(C_{1-4})$ alkylcarboxylic acid such as chloroacetic acid, bromoacetic acid, α-chloropropionic acid, α-methyl-α-chloropropionic acid, β-chloropropionic acid, α-methyl-β-chloropropionic acid, α-chlorobutyric acid, β-chlorobutyric acid, or γ-chlorobutyric acid, preferably chloroacetic acid, with hydroxyl groups of the dextran polyalcohol to achieve partial or complete carboxy$(C_{1-4})$alkylation of the hydroxyl groups.

For example, the dextran polyalcohol is dissolved in an inert solvent which does not participate in the reactions (e.g., water, N,N-dimethylformamide, or dimethyl sulfoxide) and the solution is added with a halogenated $(C_{1-4})$alkyl carboxylic acid or a salt thereof in the presence of a base (e.g., sodium hydroxide or potassium hydroxide), and then the mixture is allowed to react for several minutes to several days at a temperature under ice-cooling to about 100° C. The degree of introduction of the carboxy$(C_{1-4})$alkyl group may be easily controlled, for example, by suitably choosing the reaction temperature of the carboxy$(C_{1-4})$alkylation or the amount of the halogenated $(C_{1-4})$alkyl carboxylic acid or bases used as reagents, and these means are well-known to those skilled in the art. The degree of the carboxy$(C_{1-4})$ alkylation for hydroxyl groups of the dextran polyalcohol is not particularly limited, and for example, the degree may be in the range of from 0.01 to 2.0, preferably from 0.1 to 1.0, and more preferably from 0.3 to 0.5 per residue of the constitutive saccharide. The molecular weight of the carboxy$(C_{1-4})$alkyldextran polyalcohol is from about 5,000 to 500,000, preferably from about 50,000 to 450,000, and more preferably from about 200,000 to 400,000 when determined by the gel filtration method.

The carboxy$(C_{1-4})$alkyldextran polyalcohol prepared as above is provided as an aqueous solution of an alkali metal salt such as sodium salt or potassium salt. The method of the present invention is characterized in that an organic amine salt of the polysaccharide derivative is used, instead of the above polysaccharide derivative in the form of alkali metal salt, for the formation of the bond between the drug compound or the spacer bound to the drug compound and the carboxyl groups of the polysaccharide derivative. The organic amine salt of the polysaccharide derivatives can be dissolved at a high concentration in an organic solvent substantially free from water and enables the reaction to be carried out in a non-aqueous system, and accordingly, efficiency of the reaction can remarkably be enhanced.

As the organic amine salt, for example, salt of aliphatic amines such as triethylamine, trimethylamine, or triethanolamine; salt of alicyclic and aromatic amines such as N-methylpyrrolidine, N-methylpiperidine, N-methylmorpholine, or dimethyl-aminopyridine; or quaternary ammonium salt such as tetramethylammonium chloride or tetraethylammonium chloride can be used. The conversion from the sodium salt of the polysaccharide derivative into the organic amine salt can be carried out by using an ion exchange resin or the like. For example, sodium salt of carboxymethyldextran polyalcohol can be dissolved in water, applied to a column charged with Bio-Rad AG50W-X2 (200–400 mesh, H$^+$ type) resin, and eluted with water, and then the resulting effluent can be added with an organic amine such as triethylamine and lyophilized. Alternatively, it is also possible to carry out the conversion by one step, i.e., by dissolving the sodium salt of a carboxymethyldextran polyalcohol in water and passing the solution through triethylammonium type resin.

The bond between the drug compound, per se, and the carboxyl group of the carboxymethyldextran polyalcohol, or the bond between the spacer bound to the drug compound and the carboxyl group of the carboxymethyldextran polyalcohol can generally be formed by binding a reactive amino group of the drug compound, or the N-terminal amino group of the spacer to a carboxyl group of the carboxymethyldextran polyalcohol by means of an acid-amide bond. However, the bond between the drug compound or the spacer and the carboxyl group of the carboxymethyldextran polyalcohol is not limited to the above-described bond, and other chemical bonds and bonds utilizing one or more spacers may be used. For example, an acid anhydride may be formed between the C-terminal carboxyl group of the spacer or a carboxyl group of the drug compound and a carboxyl group of the carboxymethyldextran polyalcohol, or by using a diamine compound such as ethylenediamine used as a spacer. each of the carboxyl groups may be bound by means of an acid-amide bond to each of amino groups of the diamine compound.

When the reactive amino group substituted on the drug compound, or the N-terminal amino group of the spacer is bound to a carboxyl group of the carboxymethyldextran polyalcohol by means of an acid-amide bond, dehydration condensation agents ordinarily used for synthesis of peptide chains, for example, N,N'-dicycloalkylcarbodiimides such as N,N'-dicyclohexylcarbodiimide (DCC), carbodiimide derivatives such as 1-ethyl-3-(3-dimethylaminopropyl) carbodiimide (EDAPC), benzotriazole derivatives such as 1-hydroxybenzotriazole (HOBT), 1-ethoxycarbonyl-2-ethoxy-1,2-dihydroxyquinoline (EEDQ) and the like can be used. In addition, the reaction may also be performed by the activated ester method or the acid halide method.

The reaction may be performed in any one of organic solvents so long as they are substantially free from water and can dissolve the reactants (the organic amine salt of carboxymethyldextran polyalcohol and the drug compound or the spacer bound to the drug compound). For example, N,N-dimethylformamide, dimethyl sulfoxide, acetoamide, N-methylpyrrolidone, sulfolane and the like can be preferably used. Although the amount of the residue of the drug compound, which is introduced into the carboxymethyldextran polyalcohol by the reaction with the drug compound or the spacer bound to the drug compound, is not particularly limited, the amount should be suitably chosen from the viewpoints of, physico-chemical properties of the drug compound residue, pharmacokinetics, efficacy, and toxicity of the drug complex. Generally, the range of approximately from 0.1 to 30% by weight, and preferably approximately from 1 to 15% by weightcan be chosen. The ratio of the drug compound residue introduced into the carboxymethyldextran polyalcohol can be easily determined by, for example, absorption spectrometric analysis.

As a preferred embodiment of the preparation method of the present invention, the following scheme shows the process for introducing the oligopeptide bound to the drug compound that is the antineoplastic agent disclosed in claim 2 of the Japanese Patent Unexamined Publication (KOKAI) No. (Hei) 6-87746/1994 into a carboxymethyldextran polyalcohol. However, the methods of the present invention are not limited to those shown in the scheme. In the scheme below, the introduced amount of the residue of the drug compound is, for example, about from 1 to 15% by weight, preferably about from 4 to 8% by weight. In addition, among the constitutional units of the polyalcohols, only one constitutional unit that is introduced with one or two carboxymethyl groups is exemplified in the scheme below. However, it should be understood that the polysaccharide-derivative moiety of the drug complex is not formed by the repetition of the aforementioned constitutional unit.

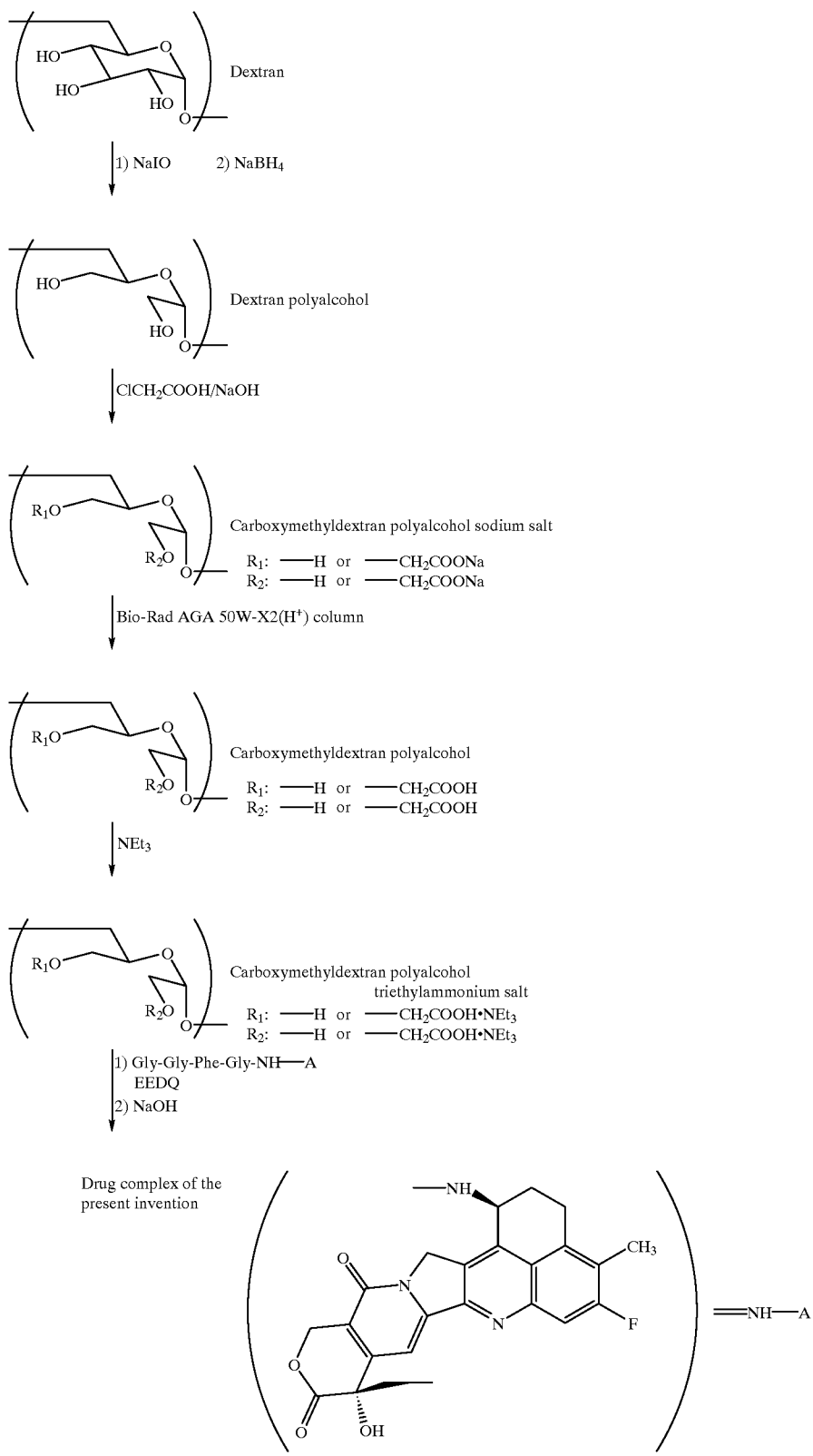

Drug Complex of the Present Invention

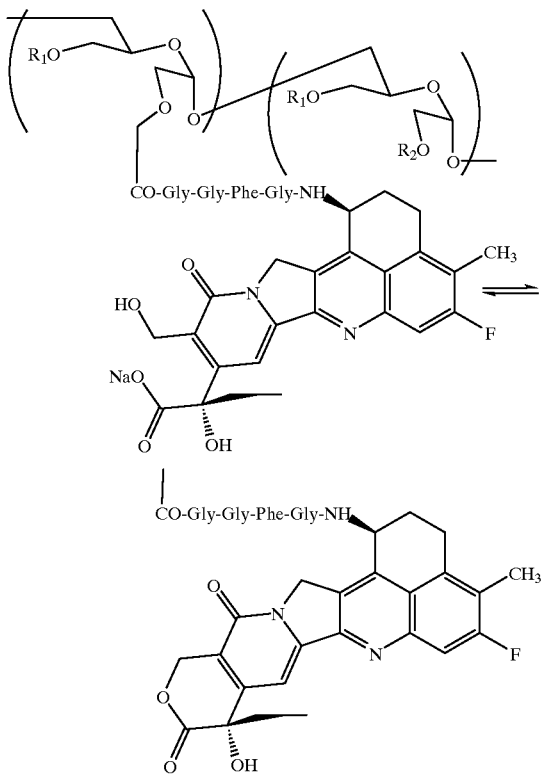

It is known that the equilibrium of the drug compound in the scheme above lies to the compound whose lactone ring is closed (the ring-closed compound) in an acidic aqueous medium (for example, approximately at pH 3), whereas the equilibrium lies to the compound whose lactone ring is opened (the ring-opened compound) in a basic aqueous medium (for example, approximately at pH 10), and the drug complex introduced with the residue corresponding to the ring-closed or ring-opened compound has similar antineoplastic activity. However, when a reactant, whose lactone ring is opened, is present in the reaction system for the reaction between the carboxymethyldextran polyalcohol and the spacer bound to the aforementioned drug compound (e.g., an oligopeptide spacer), the condensation reaction will progress between a carboxyl group derived from the lactone ring and an amino group derived from the spacer, which results in significant decrease of the reaction yield, and moreover, a desired drug complex cannot sometimes be uniformly obtained. Such side reaction can be avoided by using the ring-closed compound as the reactant in a non-aqueous system that does not allow the equilibrium. Therefore, the method of the present invention is particularly suitable for preparing the drug complex containing the aforementioned drug compound.

The aforementioned drug complex prepared according to the method of the present invention is characterized in that it can specifically exhibit desired pharmacological activity at a local site such as tumorous sites or inflammatory sites depending on the sort of the residue of the drug compound (e.g., the residue of the drug compound such as antineoplastic agents or anti-inflammatory agents), and can reduce the toxicity inherent to the drug compound, per se. For example, carboxymethyldextran polyalcohol as being the polysaccharide-derivative moiety has quite excellent retention in blood and achieves high accumulation into tumorous or inflammatory sites as a drug delivery carrier and allows the drug complex to have neoplastic site-selectivity and inflammatory site-selectivity. Furthermore, it is considered that protease (peptidase) is expressed at tumorous sites or inflammatory sites, and accordingly, the drug complex having a spacer comprising an oligopeptide is readily hydrolyzed at the spacer moiety to allow the released drug compound to exhibit its efficacy.

A medicament containing the drug complex prepared according to the method of the present invention may generally be filled in vials or the like in the form of a lyophilized product or other, and provided for clinical use as preparations for parenteral administration such as injections or drip infusions which are dissolved upon use. However, the form of pharmaceutical preparations of the medicament is not limited to the aforementioned forms. For the preparation of the above pharmaceutical preparations, pharmaceutical compositions prepared using pharmaceutical additives available in the field of the art, for example, solubilizers, pH modifiers, stabilizers and the like, can be used. Although the dose of the medicament above is not particularly limited, is should normally be decided in view of the dose of the drug compound that constitutes the residue of the drug compound, the amount of the residue of the drug compound introduced into the drug complex, the condition of a patient, the sort of a disease and the like. For example, where a drug complex is administered parenterally which is introduced with about 6% by weight of the residue of the antineoplastic agent disclosed in claim 2 of the Japanese Patent Unexamined Publication (KOKAI) No. (Hei) 6-87746/1994, about 1 to 500 mg, preferably about 10 to 100 mg per m² of body surface area per day may generally be administered once a day, and the administration may preferably repeated every 3 to 4 weeks.

EXAMPLES

The present invention will be explained more specifically by examples; however, the scope of the present invention is not limited to the following examples. In the examples, "A—NH-" represents a residue of a drug compound wherein the drug compound has a lactone ring, such as the drug compound disclosed in claim 2 of the Japanese Patent Unexamined Publication (KOKAI) No. (Hei) 6-87746/1994 (sometimes referred to as "DX-8951" in the examples), and the drug compound having a closed lactone ring is represented by A—NH$_2$. An example includes the group represented by A—NH— in the above-described scheme in which a lactone ring is formed. In addition, A'—NH— represents that the lactone ring of the residue of a drug compound represented by A—NH— is either in the ring-closed form or ring-opened form, or alternatively, a mixture thereof.

In the examples, otherwise not specifically mentioned, the degree of carboxymethylation in carboxymethyldextran polyalcohol (the degree of substitution with carboxymethyl group per constitutive saccharide residue) was determined by converting the sodium salt of the carboxymethyldextran polyalcohol into the free acid form, dissolving the resulting acid in an aqueous 0.1N sodium hydoxide solution, and then titrating by using 0.1N hydrochloric acid. An aqueous solution of the sodium salt of the carboxymethyldextran polyalcohol was applied to a Bio-Rad AG50W-x2 (H⁺ form) column and the effluent was lyophilized and then used as a sample. The sample was dissolved in a prescribed excess amount of aqueous 0.1N sodium hydroxide solution and titrated with 0.1N hydrochloric acid using phenolphthalein as an indicator. The degree of carboxymethylation was calculated by using the following equation: Degree of carboxymethylation=13.4(a-b)/[s-5.8(a-b)] wherein "s" is the weight of the applied sample (mg), "a" is the prescribed excess amount of aqueous 0.1N sodium hydroxide solution (ml), and "b" is the volume of 0.1N hydrochloric acid consumed for the titration (ml). The amount of introduced drug (percent by weight) was determined by the absorption spectroscopic analysis by using characteristic absorptions of the drug compound (approximately 362 nm). The gel filtration was performed under the following conditions: column: TSK gel G4000 PW$_{XL}$; eluent: 0.1M NaCl; flow rate: 0.8 ml/min; and column temperature: 40° C.

Example 1

3'-N-(Boc-Gly-Gly-Phe-Gly)-NH—A (A—NH$_2$=DX-8951)

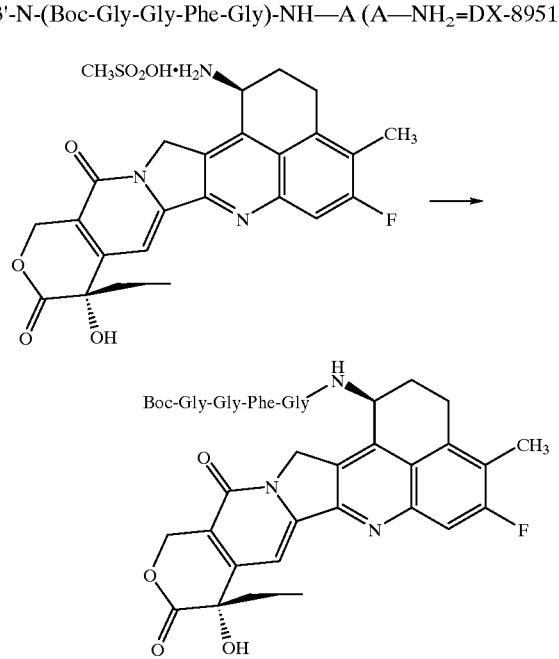

Boc-Gly-Gly-Phe-Gly (600 mg) and N-hydroxysuccinimide (160 mg) were dissolved in N,N-dimethylformamide (20 ml) and cooled to 4° C., and then added with N,N'-dicyclohexylcarbodiimide (280 mg). To this solution, a solution of methanesulfonate of the drug compound described in claim 2 of the Japanese Patent Unexamined Publication (KOKAI) No. (Hei) 6-87746/1994 (600 mg, the compound described in Example 50 of the above-mentioned patent publication) and triethylamine (0.16 ml) dissolved in N,N-dimethylformamide (30 ml) was added, and the mixture was allowed to react at room temperature for 16 hours with stirring under light-shielded conditions. This reaction mixture was evaporated to dryness under reduced pressure, and the residue was purified by silica gel column chromatography (eluent: dichloromethane:methanol=10:1 solution containing 0.5% acetic acid) to give the title compound (1.0 g).

$^1$H-NMR (DMSO-d$_6$) δ :8.40 (d,1H,J=8.3 Hz), 8.10–8.17 (m,2H), 7.91–8.01 (m,1H), 7.78 (d,1H,J=10.75 Hz), 7.32 (s,1H), 6.94–6.96 (m,1H), 6.50 (s,1H), 5.57 (t,1H,J=4.5 Hz), 5.43 (s,2H), 5.23 (s,2H), 3.77 (dd,2H,J=5.85 Hz,J=8.80 Hz), 3.70 (d,2H,J=4.40 Hz), 3.65 (d,2H,J=5.35 Hz), 3.56 (d,2H, J=5.85), 3.15–3.25 (m,2H), 2.40 (s,3H), 2.05–2.25 (m,1H), 1.86 (m,2H), 1.35 (s,9H), 0.88 (t,3H,J=7.35); Mass (FAB); m/e 854 (M+1).

Example 2

Synthesis of 3'-N-(Boc-Gly-Gly-Gly-Phe)-NH—A (A—NH$_2$=DX-8951)

Boc-Gly-Gly-Gly-Phe (600 mg) and N-hydroxysuccinimide (160 mg) were dissolved in N,N-dimethylformamide (20 ml) and cooled to 4° C., and then added with N,N'-dicyclohexylcarbodiimide (280 mg). To this solution, a solution of methanesulfonate of DX-8951 (600 mg) and triethylamine (0.16 ml) dissolved in N,N-dimethylformamide (30 ml) was added and the mixture was allowed to react at room temperature for 16 hours with stirring under light-shielded conditions. This reaction mixture was evaporated to dryness under reduced pressure, and the residue was purified by silica gel column chromatography (eluent: dichloromethane:methanol=10:1 solution containing 0.5% acetic acid) to give the title compound (700 mg).

$^1$H-NMR (DMSO-d$_6$) δ :8.57 (d,1H,J=7.8 Hz), 8.19 (d,1H), 8.05–8.07 (m,2H), 7.79 (d,1H,J=11.2 Hz), 7.32 (s,1H), 7.10 (d,2H,J=7.8 Hz), 6.93–7.03 (m,4H), 6.51 (s,1H), 5.52–5.55 (m,1H), 5.44 (s,2H), 5.18 (d,1H,J=18.5 Hz), 4.84 (d,1H,J=18.5 Hz), 4.57–4.59 (m,1H), 3.57–3.71 (m,6H), 3.15–3.25 (m,2H), 3.00–3.02 (m,1H), 2.80–2.90 (m,1H), 2.40 (s,3H), 2.05–2.25 (m,1H), 1.86 (m,2H), 1.35 (s,9H), 0.88 (t,3H,J=7.35 Hz); Mass (FAB); m/e 854 (M+1).

Example 3

Synthesis of 3'-N-(Boc-Gly-Gly-Gly-Gly)-NH—A (A—NH$_2$=DX-8951)

Boc-Gly-Gly-Gly-Gly (120 mg) and N-hydroxysuccinimide (39 mg) were dissolved in N,N-dimethylformamide (20 ml) and cooled to 4° C., and then added with N,N'-dicyclohexylcarbodiimide (70 mg). To this solution, a solution of methanesulfonate of DX-8951 (150 mg) and triethylamine (0.039 ml) dissolved in N,N-dimethylformamide (10 ml) was added, and the mixture was allowed to react at room temperature for 16 hours with stirring under light-shielded conditions. This reaction mixture was evaporated to dryness under reduced pressure, and the residue was purified by silica gel column chromatography (eluent: dichloromethane:methanol=10:1 solution) to obtain the title compound (100 mg).

$^1$H-NMR (DMSO-d$_6$) δ :8.40 (d,1H,J=8.3 Hz), 8.10–8.17 (m,2H), 7.91–8.01 (m,1H), 7.78 (d,1H,J=10.75 Hz), 7.32 (s,1H), 6.94–6.96 (m,1H), 6.50 (s,1H), 5.57 (t,1 H,J=4.5 Hz), 5.43 (s,2H), 5.23 (s,2H), 3.77 (dd,2H,J=5.85 Hz,J=8.80 Hz), 3.70 (d,2H,J=4.40 Hz), 3.65 (d,2H,J=5.35 Hz), 3.56 (d,2H,J=5.85 Hz), 3.15–3.25 (m,2H), 2.40 (s,3H), 2.05–2.25 (m,1H), 1.86 (m,2H),1.35(s,9H), 0.88 (t,3H,J=7.35 Hz); Mass (FAB); m/e 764 (M+1).

Example 4
Synthesis of 3'-N-(Gly-Gly-Gly-Gly)-NH—A (A—NH$_2$= DX-8951) Trifluoroacetate

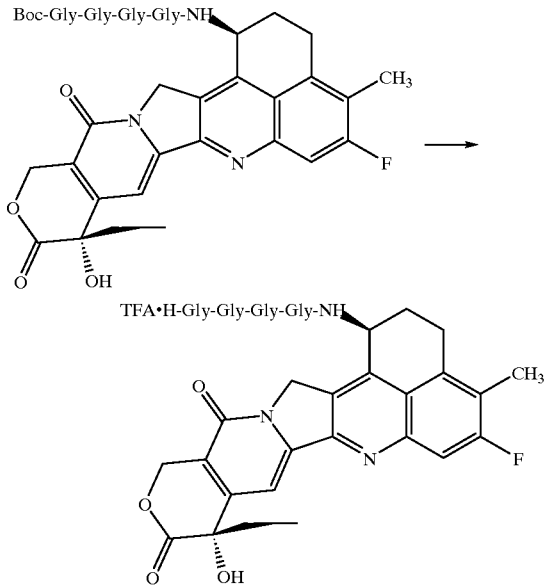

3'-N-(Boc-Gly-Gly-Gly-Gly)-NH—A (A—NH$_2$=DX-8951) (79 mg) was dissolved in trifluoroacetic acid (3 ml) and allowed to stand for one hour. The solvent was evaporated, and the residue was subjected to azeotropic distillations twice with methanol (30 ml) and twice with ethanol (30 ml), and then the residue was washed with ether to give the title compound (80 mg).

$^1$H-NMR (DMSO-d$_6$) δ :8.59–8.61 (m,1H), 8.50 (d,1H, J=8.3 Hz), 8.21–8.27 (m,2H), 7.91–8.01 (br,3H), 7.81 (d,1H, J=11.2 Hz), 7.32 (s,1H), 6.50–6.52 (br,1H), 5.57–5.59 (m,1H), 5.43 (s,2H), 5.23 (s,2H), 3.80–3.82 (m,3H), 3.70–3.75 (m,3H), 3.15–3.25 (m,2H), 2.41 (s,3H), 2.05–2.25 (m,1H), 1.86–1.88 (m,2H), 0.88 (t,3H,J=7.35 Hz).

Example 5
Synthesis of Triethylammonium salt of Carboxymethyldextran Polyalcohol Dextran T2000 (10 g, Pharmacia, average molecular weight: 2,000,000) was dissolved in 0.1M acetate buffer (pH 5.5, 1,000 ml) and added with an aqueous solution (1000 ml) of sodium periodate (33.0 g). After stirring at 4° C. for 10 days with shielding the light, the mixture was added with ethylene glycol (7.0 ml) and stirred overnight. The reaction mixture was adjusted to pH 7.5 with 8M aqueous sodium hydroxide under ice-cooling. Sodium borohydride (14 g) was added and dissolved, and the mixture was then stirred at room temperature overnight. The reaction mixture was ice-cooled, adjusted to pH 5.5 with acetic acid, and stirred at 4° C. for one hour, and then, adjusted to pH 7.5 with 8M aqueous sodium hydroxide under ice-cooling. The resulting aqueous solution was subjected to ultrafiltration using a Biomax-30 membrane (Millipore) to remove the low molecular weight fraction. The polymer fraction was lyophilized to obtain dextran polyalcohol. After treating this dextran polyalcohol at pH 3.0 for one hour, the low molecular weight fraction was removed with Biomax-50 membrane, and subsequently, the polymer fraction was removed with Biomax-100 membrane, and the result was lyophilized to give purified dextran polyalcohol (2.0 g). The molecular weight of this substance was 220K (gel filtration, dextran standard).

This purified dextran polyalcohol (1.8 g) was added to an aqueous solution obtained by dissolving sodium hydroxide (10.5 g) in water (45 ml) and dissolved at room temperature. To this solution, monochloroacetic acid (15 g) was added and dissolved under ice-cooling, and then the mixture was allowed to react at room temperature for 20 hours. After this reaction mixture was adjusted to pH 8 with acetic acid, the low molecular weight fraction was removed by ultrafiltration using a Biomax-10 membrane. The polymer fraction was lyophilized to give sodium salt of carboxymethyldextran polyalcohol (1.8 g). The molecular weight of this substance was 330K (gel filtration, dextran standard) and the degree of carboxymethylation was 0.8.

The above sodium salt of carboxymethyldextran polyalcohol (300 mg) was dissolve in water, applied to a Bio-Rad AG50W-X2 (200–400 mesh, H$^+$ form) column (1.5x8.6 cm), and eluted with water. This effluent was added with triethylamine (0.5 ml) and lyophilized to give triethylammonium salt of carboxymethyldextran polyalcohol (380 mg). Portions of the sodium salt of carboxymethyldextran polyalcohol (each 300 mg) were treated with the column as described above to give triethylammonium salt of carboxymethyldextran polyalcohol (380 mg, 400 mg).

Example 6
Synthesis of Sodium Salt of Carboxymethyldextran Polyalcohol

The sodium salt of carboxymethyldextran polyalcohol (0.15 g) obtained in Example 5 above was added to an aqueous solution obtained by dissolving sodium hydroxide (1.05 g) in water (4.5 ml) and then dissolved at room temperature. To this solution, monochloroacetic acid (1.5 g) was added and dissolved under ice-cooling, and the mixture was allowed to react at room temperature for 18 hours. This reaction mixture was adjusted to pH 8 with acetic acid, added dropwise into 90 ml of methanol, and added with 3M aqueous sodium chloride (0.15 ml), and the deposited precipitates were collected by centrifugation (3500 rpm, 8 minutes). The precipitates were washed with methanol and then dissolved in water (5 ml), and added with 3M aqueous sodium chloride (0.15 ml). This aqueous solution was filtered through a Millipore filter (0.45 μm), and the filtrate was added dropwise to 35 ml of ethanol and the deposited precipitates were collected by centrifugation (3500 rpm, 8 minutes). The precipitates were washed with ethanol, dissolved in water, and dialyzed against purified water using a dialysis membrane (Spectrapore 1, cut-off molecular weight; 6,000–8,000). The inner dialyzate solution was filtered through a Millipore filter (0.22 μm) and lyophilized to give sodium salt of carboxymethyldextran polyalcohol (0.18 g). The degree of carboxymethylation of this substance per saccharide residue was 1.2 (alkalimetry).

Example 7
Synthesis of Sodium Salt of Carboxymethyldextran Polyalcohol

The purified dextran polyalcohol (0.2 g) obtained in Example 5 was added to an aqueous solution obtained by dissolving sodium hydroxide (0.84 g) in water (6 ml) and dissolved at room temperature. To this solution, monochloroacetic acid (1.2 g) was added and dissolved under ice-cooling, and the mixture was allowed to react at room temperature for 18 hours. The reaction mixture was adjusted to pH 8 with acetic acid, added dropwise to 120 ml of methanol, and then added with 3M aqueous sodium chloride (0.2 ml), and the deposited precipitates were collected by centrifugation (3500 rpm, 8 minutes). The precipitates were washed with methanol and then dissolved in water (5 ml), and added with 3M aqueous sodium chloride (0.2 ml). This aqueous solution was filtered through a Millipore filter (0.45 μm), and the filtrate was added dropwise to 35 ml of ethanol and the precipitates deposited were collected by centrifugation (3500 rpm, 8 minutes). The precipitates were washed with ethanol, dissolved in water, and dialyzed against purified water using a dialysis membrane (Spectrapore 1, cut-off molecular weight; 6,000–8,000). The inner dialyzate solution was filtered through a Millipore filter (0.22 μm) and lyophilized to give sodium salt of carboxymethyldextran polyalcohol (0.20 g). The degree of carboxymethylation of this substance per saccharide residue was 0.4 (alkalimetry).

Example 8
Synthesis of Carboxymethyldextran Polyalcohol-Gly-Gly-Gly-Phe-NH—A' (A—NH$_2$=DX-8951)

The triethylammonium salt of carboxymethyldextran polyalcohol obtained in Example 5 (380 mg, the degree of carboxymethylation: 0.8) was dissolved in N,N-dimethylformamide (30 ml). To this solution, a solution of 3'-N-(Gly-Gly-Gly-Phe)-NH—A (A—NH$_2$=DX-8951) trifluoroacetic acid salt (49 mg) in N,N-dimethylformamide (5 ml), triethylamine (0.017 ml), and 1-ethoxycarbonyl-2-ethoxy-1,2-dihydroxyquinoline (380 mg) were added successively, and then the mixture was allowed to react at room temperature overnight with stirring. This reaction mixture was adjusted to pH 10 with 1M aqueous sodium hydroxide and each of 5 ml portions of the mixture was added dropwise to 25 ml of ethanol. This mixture was added with 3M aqueous sodium chloride (1 ml) and diethyl ether (5 ml), and the deposited precipitates were collected by centrifugation (3500 rpm, 8 minutes).

Figure 2:
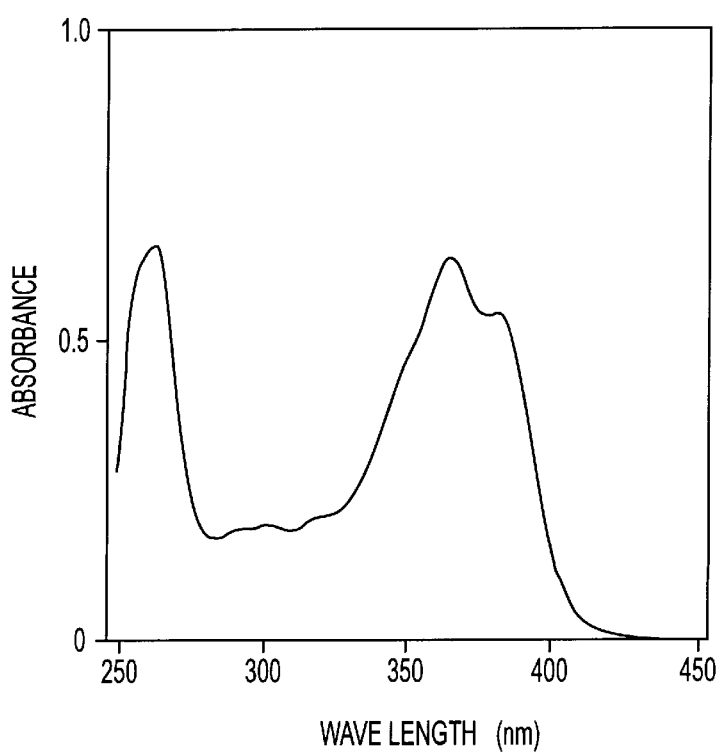
FIG. 2 shows the ultraviolet absorption spectrum of the drug complex of Example 8 prepared by the method of the present invention.

The precipitates were dissolved in water and dialyzed against purified water using a dialysis membrane (Spectrapore 1, cut-off molecular weight; 6,000–8,000), and the inner dialyzate solution was filtered through a Millipore filter (0.22 μm) and lyophilized. The resulting crude product was dissolved in water (30 ml), adjusted to pH 9 with 0.1M aqueous sodium hydroxide, and treated at 37° C. for one hour. This treated solution was dialyzed as described above, and then the inner dialyzate solution was filtered through a Millipore filter (0.22 μm) and lyophilized to give the title compound (289 mg). The result obtained by GPC analysis after dissolving this compound in 0.1M aqueous sodium chloride (column: TSK Gel PW-4000XL, Tosoh, solvent: 0.1 M NaCl, flow rate: 0.8 ml/min), and the ultraviolet absorption spectrum of the compound (0.1M Tris buffer solution, pH 9.0, 0.25 mg/ml) are shown in FIG. 1 and FIG. 2, respectively. The content of the drug compound residue in the compound was 5.3% (W/W) when determined based on the absorption at 362 nm in 0.1 M Tris buffer solution (pH 9.0).

Example 9
Synthesis of Carboxymethyldextran Polyalcohol-Gly-Gly-Phe-Gly-NH—A' (A—NH$_2$=DX-8951)

Figure 3:
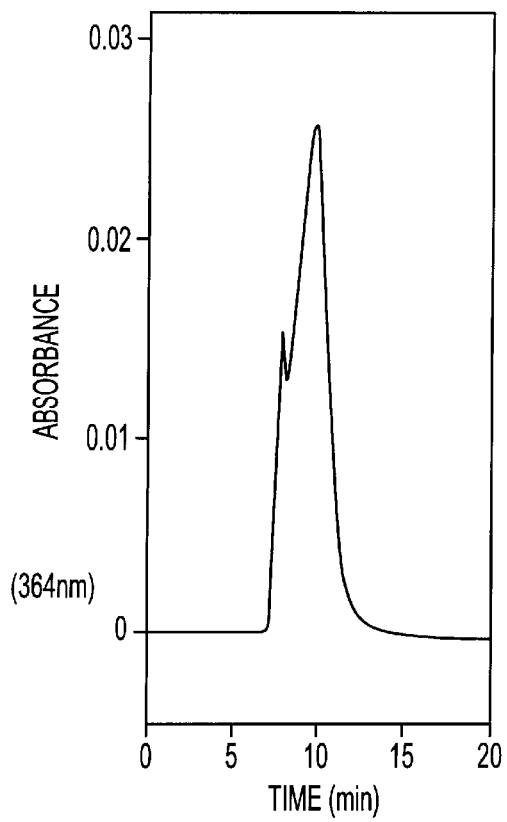
FIG. 3 shows the GPC chart of the drug complex of Example 9 prepared by the method of the present invention.
Figure 4:
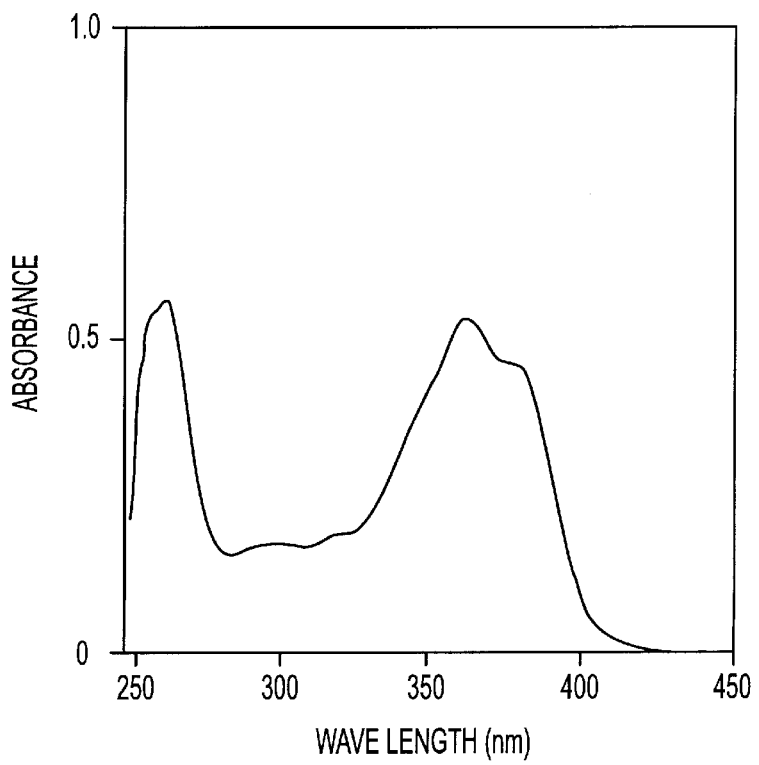
FIG. 4 shows the ultraviolet absorption spectrum of the drug complex of Example 9 prepared by the method of the present invention.

The title compound (300 mg) was synthesized according to a similar manner to that of Example 8 by introducing trifluoroacetic acid salt of 3'-N-(Gly-Gly-Phe-Gly)-NH—A, which had been obtained by removal of the Boc group from 3'-N-(Boc-Gly-Gly-Phe-Gly)-NH—A (A—NH$_2$=-DX-8951) (50 mg) in a manner similar to that of Example 4, into the triethylammonium salt of carboxymethyldextran polyalcohol (380 mg) obtained in Example 5. The result obtained by GPC analysis after dissolving this compound in 0.1M aqueous sodium chloride (column: TSK Gel PW-4000XL, Tosoh, solvent: 0.1 M NaCl, flow rate: 0.8 ml/min), and the ultraviolet absorption spectrum of the compound (0.1M Tris buffer solution, pH 9.0, 0.19 mg/ml) are shown in FIG. 3 and FIG. 4, respectively. The content of the drug compound residue in the compound was 5.3% (W/W) when determined based on the absorption at 362 nm in 0.1 M Tris buffer solution (pH 9.0).

Example 10
Synthesis of Carboxymethyldextran Polyalcohol-Gly-Gly-Gly-Gly-NH—A' (A—NH$_2$=DX-8951)

Figure 5:
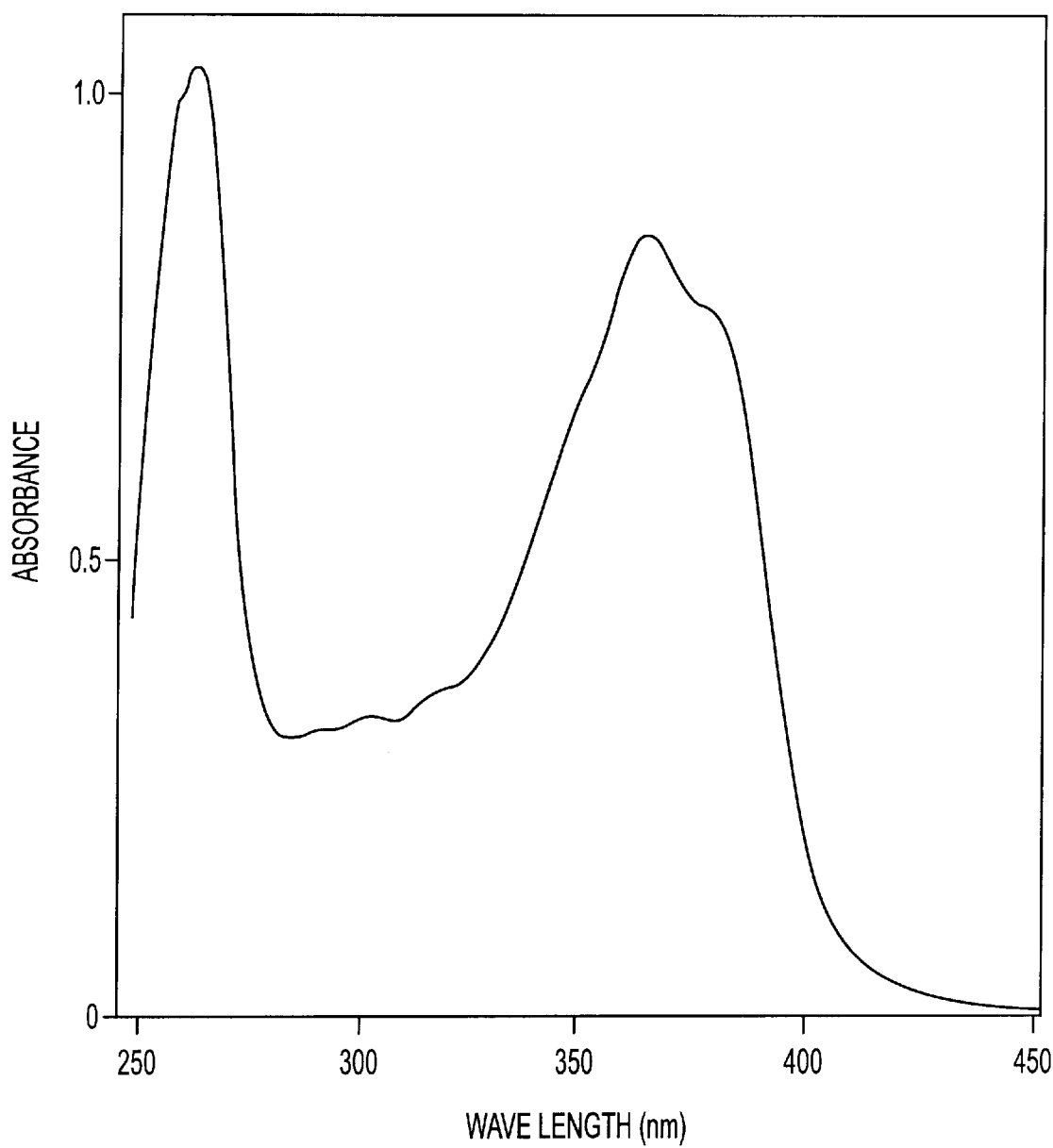
FIG. 5 shows the ultraviolet absorption spectrum of the drug complex of Example 10 prepared by the method of the present invention.

The title compound (190 mg) was synthesized according to a similar manner to that of Example 8 by introducing trifluoroacetic acid salt of 3'-N-(Gly-Gly-Gly-Gly)-NH—A, which had been obtained through removal of the Boc group from 3'-N-(Boc-Gly-Gly-Gly-Gly)-NH—A (A—NH$_2$=DX-8951) (41 mg) in a manner similar to that of Example 4, into the triethylammonium salt of carboxymethyldextran polyalcohol (380 mg) obtained in Example 5. The ultraviolet absorption spectrum of this compound (0.1M Tris buffer solution, pH 9.0, 0.34 mg/ml) is shown in FIG. 5. The content of the drug compound residue in the compound was 5.3% (W/W) when determined based on the absorption at 362 nm in 0.1 M Tris buffer solution (pH 9.0).

Example 11
Antitumor Activity of the Drug Complex of the Present Invention

Meth A tumor-bearing mice were prepared (7 mice per group) by subcutaneously transplanting 1×10$^6$ mouse fibrosarcoma Meth A cells into the right inguinal regions of BALB/c male mice (7-week old). On day 7, the drug complex of Example 9 dissolved in distilled water for injection was injected in the tail vein of the Meth A tumor-bearing mice every 4 days 4 times. On day 21 after the transplantation, tumor masses were excised and weighed to calculate the inhibition rate of tumor growth according to the following equation: inhibition rate of tumor growth (%)= [1−(average tumor weight of the group administered with the test sample/average tumor weight of control group)]× 100. As a result, it was found that the drug complex of the present invention obtained in Example 9 exhibited remarkably enhanced antitumor activity compared to the drug compound, per se, without the spacer and the polysaccharide derivative, while showing no toxicity (weight loss). The polysaccharide derivative (Example 5), per se, and the drug compound introduced solely with the spacer (trifluoroacetic acid salt of H)N-Gly-Gly-Phe-Gly-NH—A (A—NH$_2$=DX-8951) obtained by removing the Boc group from the compound of Example 1 according to the process of Example 4) were found to be not effective.

TABLE 2

| Test compound | Dose (mg/kg) | Inhibition rate (%) |
|---|---|---|
| Drug compound, per se | 7.5 × 4 | 76 |
|  | 1.875 × 4 | 46 |
|  | 0.9375 × 4 | 36 |
| Compound of Example 9 | 1.4[1] × 4 | 94 |
|  | 0.7[1] × 4 | 59 |
|  | 0.35[1] × 4 | 41 |

[1]Calculated based on the drug compound

Example 12
Antitumor Activity of the Drug Complex of the Present Invention

Meth A tumor-bearing mice (6 mice per group) were prepared according to a similar manner to that of Example 11 and the antitumor activity was compared to that obtained by single administration of the drug complexes of Examples 8 and 9 once on day 7. As a result, the degree of the antitumor activity was as follows: (Polysaccharide derivative)-Gly-Gly-Phe-Gly-NH—A'> (Polysaccharide derivative)-Gly-Gly-Gly-Phe-NH—A'> the drug compound, per se. The compound comprising the residue of the drug compound directly binding to a carboxyl group of the carboxymethyldextran polyalcohol of Example 5 without any spacer (the amount of the drug compound residue introduced: 6.2% by weight) was found to be not effective.

TABLE 3

| Test compound | Dose (mg/kg) | Inhibition rate (%) |
| --- | --- | --- |
| Drug compound itself | 60 | 77 |
|  | 20 | 59 |
| Compound of Example 8 | 10[1] | 85 |
|  | 5[1] | 76 |
| Compound of Example 9 | 5[1] | 98 |
|  | 2.5[1] | 87 |

[1]Calculated based on the drug compound

Example 13
Synthesis of Triethylam Monium Salt of Carboxymethyldextran Polyalcohol Dextran T500 (10 g, Pharmacia, molecular weight: 500K) was dissolved in 0.1M acetate buffer (pH 5.5, 1000 ml) and added with an aqueous solution (1000 ml) of sodium periodate (33 g). After stirring at 4° C. for ten days with shielding the light, the mixture was added with ethylene glycol (7.0 ml) and stirred overnight. The reaction mixture was adjusted to pH 7.5 with 8M aqueous sodium hydroxide. Sodium borohydride (14 g) was added and dissolved, and then the mixture was stirred overnight The reaction mixture was ice-cooled, adjusted to pH 5.5 with acetic acid and stirred at 4° C. for one hour, and then adjusted to pH 7.5 with 8M aqueous sodium hydroxide to give Solution 1. Separately, a series of procedures described above was performed using Dextran T500 (10 g, Pharmacia, molecular weight 500K) to obtain Solution 2. Furthermore, a series of procedures described above was repeated by using Dextran T250 (10 g each, Pharmacia, molecular weight 250K) to obtain Solution 3 and Solution 4. These Solutions 1–4 were combined and subjected to ultrafiltration using a Biomax-50 membrane to remove the low molecular weight fraction. The polymer fraction was lyophilized to give dextran polyalcohol (25 g). The molecular weight of this substance was 163K (gel filtration, pullulan standard).

This dextran polyalcohol (11 g) was added to an aqueous solution obtained by dissolving sodium hydroxide (46.2 g) in water (330 ml) and dissolved at room temperature. To this solution, monochloroacetic acid (66 g) was added under ice-cooling and dissolved, and the mixture was allowed to react at room temperature overnight. This reaction mixture was adjusted to pH 9 with acetic acid and desalted by ultrafiltration using a Biomax-30 membrane. The remaining solution that had not passed through the membrane was lyophilized to obtain sodium salt of carboxymethyldextran polyalcohol (13 g). The molecular weight of this substance was 228K (gel filtration, pullulan standard) and the degree of carboxymethylation was 0.4.

This sodium salt of carboxymethyldextran polyalcohol (600 mg) was dissolved in water, applied to a Bio-Rad AG 50W-X2 (200–400 mesh, H$^+$ form) column (diameter: 44 mm, length: 210 mm), and eluted with water. This effluent was added with triethylamine (0.93 ml) and then lyophilized to give the title compound (690 mg).

Example 14
Synthesis of 3'-N-(Gly-Gly-Phe-Gly)-NH—A (A—NH$_2$=DX-8951) Trifluoroacetic Acid Salt The 3'-N-(Boc-Gly-Gly-Phe-Gly)-NH—A (A—NH$_2$=DX-8951) (79 mg) obtained in Example 1 was dissolved in trifluoroacetic acid (3 ml) and allowed to stand for one hour. The solvent was evaporated, and the residue was subjected to azeotropic distillation twice with methanol (30 ml) and twice with ethanol (30 ml), and then washed with ether to give the title compound (80 mg).

$^1$H-NMR (DMSO-d$_6$) δ :8.53 (d, 1H, J=8.3 Hz), 8.40–8.48 (m, 2H), 8.28 (d, 1H, J=8.3 Hz), 7.95–8.07 (br, 3H), 7.81 (d, 1H, J=10.2 Hz), 7.30–7.37 (m, 2H), 7.15–7.30 (m, 5H), 6.50–6.55 (br, 1H), 5.50–5.57 (m, 1H), 5.41 (d, 2H, J=7.82 Hz), 5.25 (s, 2H), 4.55–4.62 (m, 1H), 3.55–3.92 (m, 6H), 3.15–3.25 (br, 2H), 2.98–3.03 (m, 1H), 2.73–2.82 (m, 1H), 2.40 (s, 3H), 2.05–2.25 (m1, H), 1.84–1.92 (m, 2H), 0.88 (t, 3H, J=7.35 Hz).

Example 15
Synthesis of Carboxymethyldextran Polyalcohol-Gly-Gly-Phe-Gly-NH—A' (A—NH$_2$=DX-8951)

The sodium salt of carboxymethyldextran polyalcohol obtained in Example 13 (400 mg) was converted into the triethylammonium salt (470 mg) and dissolved in N,N-dimethylformamide (30 ml). To this solution, a solution of trifluoroacetic acid salt of 3'-N-(Gly-Gly-Phe-Gly)-NH—A (A—NH$_2$=DX-8951) obtained in Example 14 (62 mg) in N,N-dimethylformamide (5 ml), triethylamine (0.02 ml), and 1-ethoxycarbonyl-2-ethoxy-1,2-dihydroxyquinoline (470 mg) were added successively, and the mixture was allowed to react at room temperature overnight with stirring and shielding the light.

Figure 6:
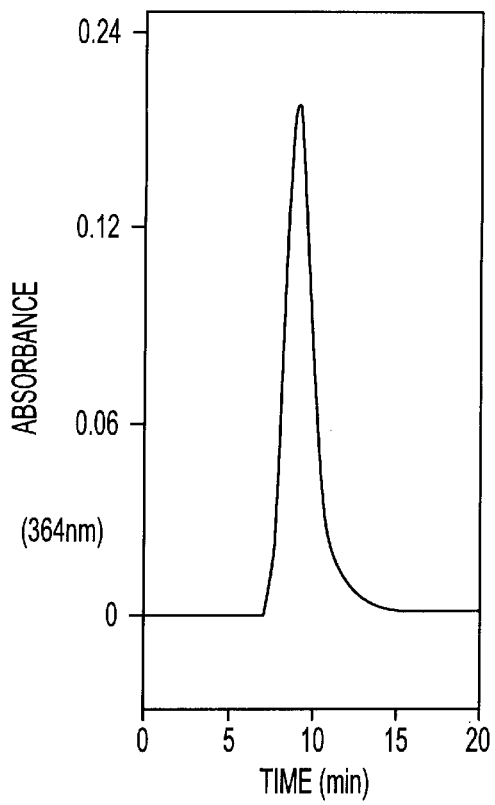
FIG. 6 shows the GPC chart of the drug complex of Example 15 prepared by the method of the present invention.
Figure 7:
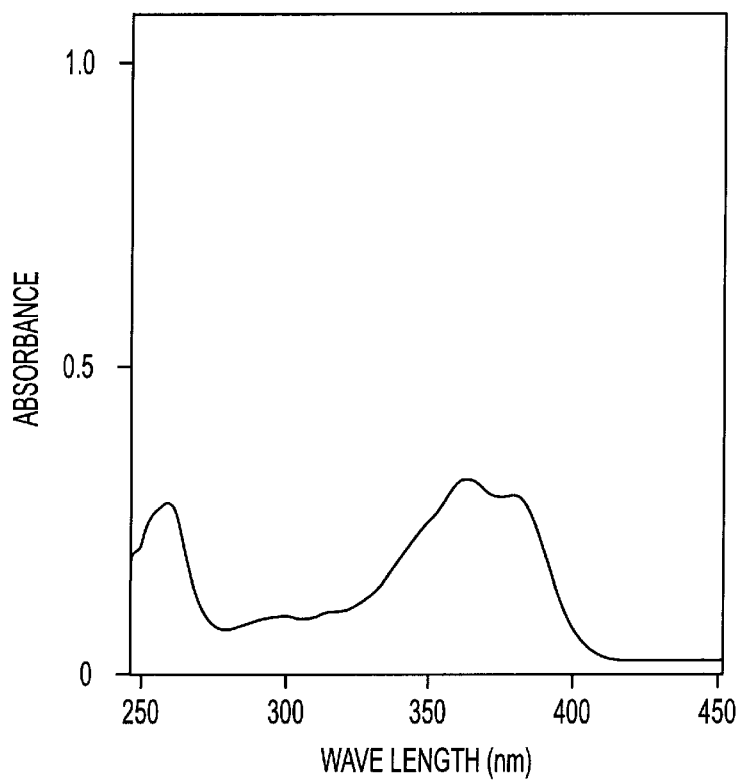
FIG. 7 shows the ultraviolet absorption spectrum of the drug complex of Example 15 prepared by the method of the present invention.

Each of 5 ml portions of this reaction mixture was added dropwise to each 10 ml of ethanol. To the mixture, 3M aqueous sodium chloride (2.5 ml) and diethyl ether (20 ml) were added, and the precipitates deposited were collected by centrifugation. The precipitates were dissolved in 0.5M aqueous sodium chloride, adjusted to pH 9 with 0.1M aqueous sodium hydroxide under ice-cooling and then dialyzed against purified water using a dialysis membrane (Spectrapore 1, cut-off molecular weight; 6,000–8,000). The inner dialyzate solution was filtered through a Millipore filter (0.22 μm) and then lyophilized to obtain the title compound (600 mg). The result obtained by GPC analysis after dissolving this compound in 0.1M aqueous sodium chloride (column: TSK Gel PW-4000XL, Tosoh; solvent: 0.1 M NaCl; flow rate: 0.8 ml/min) and the ultraviolet absorption spectrum of the compound (0.1M Tris buffer solution, pH 9.0, 0.1 mg/ml) are shown in FIG. 6 and FIG. 7, respectively. The content of the drug compound residue in the compound was 5.8% (W/W) when determined based on the absorption at 362 nm in 0.1 M Tris buffer solution (pH 9.0).

Example 16
Synthesis of 3'-N-(Gly-Gly-Gly-Phe)-NH—A (A—NH$_2$=DX-8951) Trifluoroacetic Acid Salt The 3'-N-(Boc-Gly-Gly-Gly-Phe)-NH—A (A—NH$_2$=DX-8951) (79 mg) obtained in Example 2 was dissolved in trifluoroacetic acid (3 ml) and allowed to stand for one hour. The solvent was evaporated, and the residue was subjected to azeotropic distillation twice with methanol (30 ml) and twice with ethanol (30 ml), and then the residue was washed with ether to give the title compound (80 mg).

$^1$H-NMR (DMSO-d$_6$) δ :8.62–8.66 (m, 2H), 8.23 (d, 1H, J=8.3 Hz), 8.18–8.20 (m, 1H), 7.98–8.10 (br, 2H), 7.79 (d, 1H, J=10.7 Hz), 7.32 (s, 1H), 7.09 (d, 2H, J=7.3 Hz), 6.93–7.03 (m, 4H), 6.50–6.60 (br,1H), 5.52–5.55 (m, 1H), 5.44 (s, 2H), 5.18 (d, 1H, J=18.5 Hz), 4.80 (d, 1H, J=18.5 Hz), 4.57–4.59 (m, 1H), 3.57–3.71 (m, 6H), 3.15–3.25 (m, 2H), 3.00–3.02 (m, 1H), 2.80–2.90 (m, 1H), 2.50 (s, 3H), 2.05–2.25 (m, 1H), 1.86–2.00 (m, 2H), 0.88 (t, 3H, J=7.35 Hz).

Example 17
Synthesis of Carboxymethyldextran Polyalcohol-Gly-Gly-Gly-Phe-NH—A' (A—$NH_2$=DX-8951)

The sodium salt of carboxymethyldextran polyalcohol obtained in Example 13 (1.0 g) was converted into the triethylammonium salt (1.2 g) and dissolved in N,N-diethylformamide (90 ml). To this solution, a solution of trifluoroacetic acid salt of 3'-N-(Gly-Gly-Gly-Phe)-NH—A (A—$NH_2$=DX-8951) obtained in Example 16 (158 mg) in N,N-dimethylformamide (15 ml), triethylamine (0.05 ml), and 1-ethoxycarbonyl-2-ethoxy-1,2-dihydroxyquinoline (1.2 g) were added successively, and the mixture was allowed to react at room temperature overnight with stirring and shielding the light. Each of 5 ml portions of this reaction mixture was added dropwise to each 10 ml of ethanol. The mixture was added with 3M aqueous sodium chloride (2.5 ml) and diethyl ether (20 ml), and then the precipitates deposited were collected by centrifugation. The precipitates were dissolved in 0.5M aqueous sodium chloride, adjusted to pH 9 with 0.1M aqueous sodium hydroxide under ice-cooling and dialyzed against purified water using a dialysis membrane (Spectrapore 1, cut-off molecular weight; 6,000–8,000). The inner dialyzate solution was filtered through a Millipore filter (0.22 μm) and then lyophilized to obtain the title compound (1.4 g). The content of the drug compound residue in this compound was 5.2% (W/W) when determined based on the absorption at 362 nm in 0.1 M Tris buffer solution (pH 9.0).

Example 18
Synthesis of Boc-Gly-Phe-Leu-OH

H-Gly-Phe-Leu-OH (3.0 g) was added to 50% aqueous dioxane (48 ml) and ice-cooled. To this solution, 1N aqueous sodium hydroxide (9.45 ml) and a dioxane solution (24 ml) containing (Boc)$_2$O (2.27 g) were added, and the mixture was stirred overnight. 1N hydrochloric acid (9.45 ml) was added to the reaction mixture and the solvent was evaporated. The resulting residue was purified by silica gel column chromatography (eluent: dichloromethane:methanol=5:1 solution) to obtain the title compound (2.5 g).

Example 19
Synthesis of Boc-Gly-Phe-Leu-Gly-OBzl

The Boc-Gly-Phe-Leu-OH obtained in Example 18 (2.4 g) and N-hydroxysuccinimide (656 mg) were dissolved in N,N-dimethylformamide (50 ml), cooled to 4° C., and then added with N,N'-dicyclohexylcarbodiimide (1.17 g), and stirred for 2 hours. To this solution, a N,N-dimethylformamide solution (40 ml) in which tosylate of H-Gly-OBzl (1.9 g) and triethylamine (0.79 ml) had been dissolved was added, and the mixture was allowed to react with stirring at room temperature for 16 hours. This reaction mixture was evaporated to dryness under reduced pressure, and the residue was purified by silica gel column chromatography (eluent: dichloromethane:methanol=50:1 solution) to give the title compound (2.0 g).

$^1$H-NMR (DMSO-d$_6$) δ : 8.20–8.30 (m, 1H), 8.12 (d, 1H, J=8.3 Hz), 7.83 (d, 1H, J=8.3 Hz), 7.32–7.37 (m, 5H), 6.89–6.95 (m, 1H), 5.12 (s, 1H), 4.52–4.59 (br, 1H), 4.34 (dd, H, J=7.3 Hz, J=15.1 Hz), 3.93 (dd, 1H, J=5.5 Hz, J=17.2 Hz), 3.84 (dd, 1H, J=5.5 Hz, J=17.2 Hz), 3.54 (dd, 1H, J=5.9 Hz, J=16.7 Hz), 3.42 (dd, J=5.9 Hz, J=16.7 Hz), 3.00 (dd, 1H, J=4.4 Hz, 13.7 Hz), 2.78 (dd, 1H, J=8.8 Hz, J=13.2 Hz), 1.50–1.65 (m, 1H), 1.45 (t, 2H, J=7.3 Hz), 1.36 (s, 9H), 0.86 (d, 3H, J=6.4 Hz), 0.82 (d, 3H, J=6.4 Hz).

Example 20
Synthesis of Boc-Gly-Phe-Leu-Gly-OH

The Boc-Gly-Phe-Leu-OBzl (1.7 g) obtained in Example 19 was dissolved in a mixed solution of ethyl acetate (30 ml) and methanol (30 ml), and added with 5% Pd-C (1.5 g) to perform catalytic reduction. The reaction mixture was filtered and the filtrate was evaporated to dryness under reduced pressure to give the title compound (1.15 g).

Example 21
Synthesis of 3'-N-(Boc-Gly-Phe-Leu-Gly)-NH—A (A—$NH_2$=DX-8951)

The Boc-Gly-Phe-Leu-Gly-OH obtained in Example 20 (200 mg) and N-hydroxysuccinimide (58 mg) were dissolved in N,N-dimethylformamide (5 ml). After cooling at 4° C., N,N'-dicyclohexylcarbodiimide (104 mg) was added to the solution and dissolved. To this solution, a N,N-dimethylformamide solution (5 ml) in which methanesulfonate of DX-8951 (224 mg) and triethylamine (0.059 ml) had been dissolved was added, and the mixture was allowed to react with stirring at room temperature for 16 hours under light-shielded conditions. This reaction mixture was evaporated to dryness under reduced pressure, and the residue was purified by silica gel column chromatography (eluent: dichloromethane:methanol=10:1 solution containing 0.5% acetic acid) to give the title compound (200 mg).

$^1$H-NMR (DMSO-d;) δ : 8.35 (d, 1H, J=7.8 Hz), 8.08–8.18 (m, 2H), 7.75–7.85 (m, 2H), 7.32 (s, 1H), 7.10 (d, 2H, J=6.8 Hz), 7.08–7.13 (m, 3H), 6.85–6.95 (br, 1H), 6.40–6.65 (br, 1H), 5.52–5.55 (m, 1H), 5.46 (d, 1H, J=18.5 Hz), 5.37 (d, 1H, J=18.5 Hz), 5.24 (s,2H), 4.44–4.52 (m, 1H), 4.15–4.25 (m, 1H), 3.68–3.72 (m, 2H), 3.40–3.52 (m, 2H), 3.15–3.25 (br, 2H), 2.85–2.95 (m, 1H), 2.65–2.75 (m, 1H), 2.40 (s, 3H), 2.05–2.25 (m, 1H), 1.80–1.91 (m, 2H), 1.50–1.65 (m, 1H), 1.45 (t, 2H, J=7.3 Hz), 1.35 (s, 9H), 0.88 (t, 3H, J=7.4),0.86 (d, 3H, J=6.4 Hz), 0.82 (d, 3H, J=6.4 Hz).

Example 22
Synthesis of 3'-N-(Gly-Phe-Leu-Gly)-NH—A (A—$NH_2$=DX-8951) Trifluoroacetic Acid Salt The 3'-N-(Boc-Gly-Phe-Leu-Gly)-NH—A (A—$NH_2$=DX-8951) (97 mg) obtained in Example 21 was dissolved in trifluoroacetic acid (3 ml) and allowed to stand for one hour. The solvent was evaporated, and the residue was subjected to azeotropic distillation twice with methanol (30 ml) and twice with ethanol (30 ml), and then washed with ether to obtain the title compound (95 mg).

$^1$H-NMR (DMSO-d$_6$) δ : 8.57 (d, 1H, J=8.3 Hz), 8.47 (d, 1H, J=8.3 Hz), 8.32 (d, 1H, J=7.8 Hz), 8.17 (t, 1H, J=5.5 Hz), 7.81–7.91 (br, 3H), 7.79 (d, 1H, J=10.7 Hz), 7.32 (s, 1H), 7.21–7.23 (m, 5H), 7.12–7.17 (m, 1H), 6.45–6.55 (br, 1H), 5.57 (q, 1H, J=4.4 Hz), 5.43 (d, 1H, J=16.1 Hz), 5.34 (d, 1H, J=16.1 Hz), 5.23 (s, 2H), 4.67 (dt, 1H, J=4.0 Hz, J=9.0 Hz), 4.31 (dd, 1H, J=8.5 Hz, J=15.0 Hz), 4.0–4.4 (br, 1H), 3.74–3.76 (m, 2H), 3.56 (dd, 1H, J=6.0 Hz, J=16.0 Hz), 3.41 (dd, 1H, J=6.0 Hz, J=16.0 Hz), 3.17–3.19 (br, 2H), 3.02 (dd, 1H, J=4.0 Hz, J=14.0 Hz), 2.70 (dd, 1H, J=10.0 Hz, J=14.0 Hz), 2.40 (s, 3H), 2.05–2.15 (m, 1H), 1.85 (dt, 2H, J=7.0 Hz, J=14.0 Hz), 1.50–1.55 (m, 1H), 1.45 (t, 2H, J=6.0 Hz), 1.35 (s, 9H), 0.88 (t, 3H, J=7.4), 0.85 (d, 3H, J=6.4 Hz), 0.80 (d, 3H, J=6.4 Hz).

Example 23
Synthesis of Carboxymethyldextran Polyalcohol-Gly-Phe-Leu-Gly-NH—A' (A—NH$_2$=DX-8951)

The triethylammonium salt of carboxymethyldextran polyalcohol obtained in Example 13 (690 mg) was dissolved in N,N-dimethylformamide (50 ml). To this solution, a solution of the trifluoroacetic acid salt of 3'-N-(Gly-Phe-Leu-Gly)-NH—A (A—NH$_2$=DX-8951) (95 mg) obtained in Example 22 in N,N-dimethylformamide (10 ml), triethylamine (0.03 ml), and 1-ethoxycarbonyl-2-ethoxy-1,2-dihydroxyquinoline (690 mg) were added successively, and the mixture was allowed to react at room temperature overnight with stirring. Each of 5 ml portions of this reaction mixture was added dropwise to each 10 ml of ethanol. The mixture was added with 3M aqueous sodium chloride (2.5 ml) and diethyl ether (20 ml), and the deposited precipitates were collected by centrifugation. The precipitates were dissolved in 0.5M aqueous sodium chloride, adjusted to pH 9 with 0.1M aqueous sodium hydroxide, and dialyzed against purified water using a dialysis membrane (Spectrapore 1, cut-off molecular weight; 6,000–8,000). The inner dialyzate solution was filtered through a Millipore filter (0.22 μm), and then the filtrate was lyophilized to obtain the title compound (600 mg). The content of the drug compound residue in this compound was 4.8% (W/W) when determined based on the absorption at 362 nm in 0.1 M Tris buffer solution (pH 9.0).

Example 24
Synthesis of Triethylammonium Salt of Carboxymethyldextran Polyalcohol Dextran T500 (50 g, Pharmacia, molecular weight: 500K) was dissolved in 0.1M acetate buffer (pH 5.5, 5000 ml), and an aqueous solution (5000 ml) of sodium periodate (165.0 g) was added. After stirring at 4° C. for ten days with shielding the light, the mixture was added with ethylene glycol (35.0 ml) and stirred overnight. The reaction mixture was adjusted to pH 7.5 with 8M aqueous sodium hydroxide.

Sodium borohydride (70 g) was added and dissolved, and then the mixture was stirred overnight. The reaction mixture was ice-cooled, adjusted to pH 5.5 with acetic acid and stirred at 4° C. for one hour, and then adjusted to pH 7.5 with 8M aqueous sodium hydroxide. The resulting solution was subjected to ultrafiltration using a Biomax-50 membrane to remove the low molecular weight fraction. The polymer fraction was lyophilized to obtain dextran polyalcohol (27.1 g). The molecular weight of this substance was 140K (gel filtration, pullulan standard).

This dextran polyalcohol (5 g) was added to an aqueous solution obtained by dissolving sodium hydroxide (21 g) in water (150 ml), and dissolved at room temperature. To this solution, monochloroacetic acid (30 g) was added under ice-cooling and dissolved, and then the mixture was allowed to react at room temperature overnight. This reaction mixture was adjusted to pH 8 with acetic acid and then desalted by ultrafiltration using a Biomax-50 membrane. The remaining solution that had not passed through the membrane was lyophilized to obtain sodium salt of carboxymethyldextran polyalcohol (5.6 g). The molecular weight of this substance was 263K (gel filtration, pullulan standard) and the degree of carboxymethylation was 0.4.

This sodium salt of carboxymethyldextran polyalcohol (2.0 g) was dissolved in water, applied to a Bio-Rad AG 50W-X2 (200–400 mesh, H$^+$ form) column (diameter: 44 mm, length: 210 mm), and eluted with water. This effluent was added with triethylamine (4 ml) and lyophilized to obtain the title compound (2.2 g).

Example 25
Synthesis of Trimethylammonium Salt of Carboxymethyldextran Polyalcohol The sodium salt of carboxymethyldextran polyalcohl (1.0 g) obtained in Example 24 was dissolved in water, applied to a Bio-Rad AG 50W-X2 (200–400 mesh, Me$_3$N H$^+$ form) column, and eluted with water. This effluent was lyophilized to obtain the title compound (950 mg).

Example 26
Synthesis of 3'-N-(Gly-Gly-Phe-Gly)-NH—A (A—NH$_2$=DX-8951) Hydrochloride In a manner similar to that of Example 14, 3'-N-(Gly-Gly-Phe-Gly)-NH—A trifluoroacetic acid salt obtained from 3'-N-(Boc-Gly-Gly-Phe-Gly-(NH—A (A—NH$_2$=DX-8951) (400 mg) was dissolved in water/NeOH (1:4), applied to a Bio-Rad AG 1-X8 (200–400mesh, Cl$^-$ form) column (1.5cm×8.6cm), and eluted with the above solvent. This effluent was concentrated and then lyophilized to obtain the title compound (310 mg).

$^1$H-NMR (DMSO-d$_6$) δ : 8.53 (d, 1H, J8.5 Hz), 8.46–8.48 (m, 1H), 8.37–8.39 (m, 1H), 7.95 (d, 1H, J=8.0 Hz), 7.80 (s, 3H), 7.78 (d, 1H, J=11.1 Hz), 7.34 (s, 1H), 7.14–7.24 (m, 5H), 6.50(s, 1H), 5.56–5.60 (m, 1H), 5.35–5.40 (m, 2H), 5.24 (s, 2H), 4.51–4.56 (m, 1H), 3.86 (dd, J=4.8, 13.5 Hz, 1H), 3.68–3.79 (m, 3H), 3.54 (s, 2H), 3.15–3.22 (m, 2H), 3.01 (dd, J=5.6, 13.5 Hz, 1H), 2.78 (dd, J=9.6, 3.5 Hz, 1H), 2.41 (s, 3H), 2.12–2.23 (m, 2H), 1.81–1.89 (m, 2H), 0.88 (t, 3H, J=7.2 Hz); Mass (FAB); m/e 753 (M+1).

Example 27
Synthesis of Carbothaoldextran Polyalcohol-Gly-Gly-Phe-Gly-NH—A' (A—NH$_2$=DX-8951)

The trimethylammonium salt of carboxymethyldextran polyalcohol obtained in Example 25 (0.1 g) was dissolved in N,N-dimethylformamide (6 ml). To this soution, a solution of the hydrochloride of 3'-N-(Gly-Gly-Phe-Gly)-NH—A (A—NH$_2$=DX-8951) (24 mg) obtained in Example 26 in N,N-dimethylformamide (10 ml), triethylamine (5 μl), and 1-ethoxycarbonyl-2-ethoxy-1,2- dihydroxyquinoline (0.1 g) were added successively, and the mixture was allowed to react at room temperature overnight with stirring. Each of 5 ml portions of this reaction mixture was added dropwise to each 10 ml of ethanol. The mixture was added with 3M aqueous sodium chloride (2.5 ml) and diethyl ether (20 ml), and the deposited precipitates were colected by centrifugation (3500 rpm, 8 minutes). The precipitates were dissolved in 0.5M aqueous sodium chloride and adjust ed to pH 9 with 0.1M aqueous sodium hydroxide under ice-cooling. The resulting aqueous solution was desalted by ultrafiltration using a Biomax-30 membrane. The remaining solution that had not passed through the membrane was filtered through a Millipore filter (0.22 μm) and then lyophilized to give the title compound (90 mg). The content of the d rug compound residue in this compound was 11% (W/W) when determined based on the absorption at 362 nm in 0.1M Tris buffer solution (pH 9.0).

Example 28
Synthesis of Carboxmmethyldextran Polyalcobol-Gly-Gly-Phe-Gly-NH—A' (A—NH$_2$=DX-8951)

Figure 8:
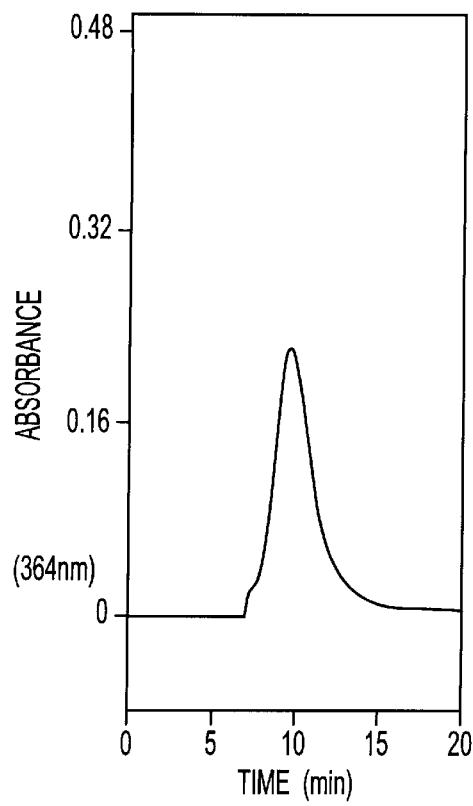
FIG. 8 shows the GPC chart of the drug complex of Example 28 prepared by the method of the present invention.
Figure 9:
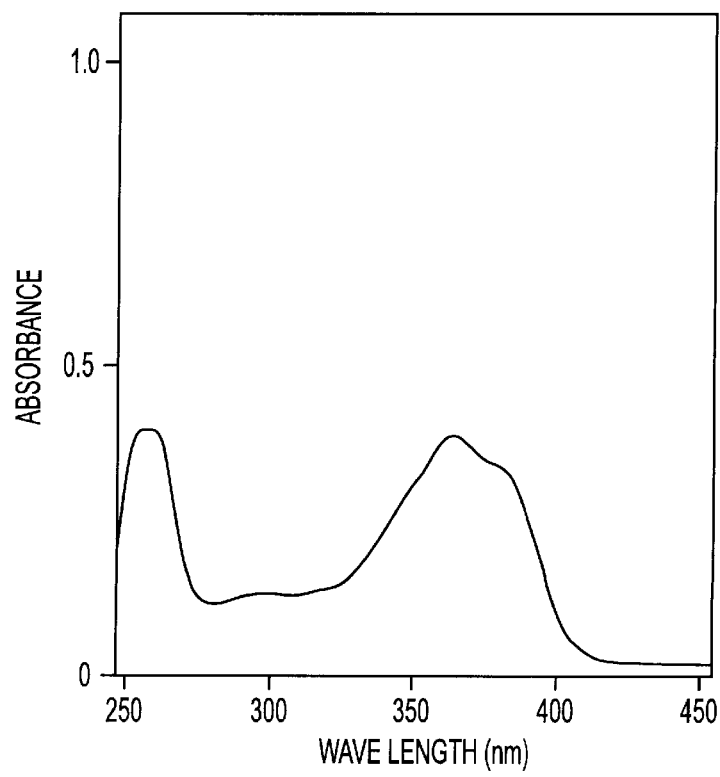
FIG. 9 shows the ultraviolet absorption spectrum of the drug complex of Example 28 prepared by the method of the present invention.

The trimethylammonium salt of carboxymethyldextran polyalcohol obtained in Example 25 (0.1 g) was dissolved in N,N-dimetsylformamide (6 ml). To this solution, a solution of the 3'-N-(Gly-Gly-Phe-Gly)-NH—A (A—NH$_2$=DX-8951) hydrochloride (36 mg) obtained in Example 26 in N,N-dimethylformamide (10 ml), triethylamine (8 μl), and 1-ethoxycarbonyl-2-ethoxy-1,2-dihydroxyquinoline (0.1 g)

were added successively, and the mixture was allowed to react at room temperature overnight with stirring. Each of 5 ml portions of this reaction mixture was added dropwise to each 10 ml of ethanol. The mixture was added with 3M aqueous sodium chloride (2.5 ml) and diethyl ether (20 ml), and the precipitates deposited were collected by centrifugation (3500 rpm, 8 minutes). The precipitates were dissolved in 0.5M aqueous sodium chloride and adjusted to pH 12 with 0.1M aqueous sodium hydroxide under ice-cooling. The resulting aqueous solution was desalted by ultrafiltration using a Biomax-30 membrane. The remaining solution that had not passed through the membrane was filtered through a Millipore filter (0.22 μm) and then lyophilized to give the title compound (80 mg). The result obtained by GPC analysis after dissolving this compound in 1.0M aqueous sodium chloride (column: TSK Gel PW-4000XL, Tosoh, solvent: 0.1 M NaCl, flow rate: 0.8 ml/min), and the ultraviolet absorption spectrum of the compound (0.1M Tris buffer solution, pH 9.0, 36 μg/ml) are shown in FIG. 8 and FIG. 9, respectively. The content of the drug compound residue in the compound was 15% (W/W) when determined based on the absorption at 362 nm in 0.1 M Tris buffer solution (pH 9.0).

Example 29
Synthesis of Carboxymethyldextran Polyalcohol-Gly-Gly-Gly-Phe-NH—A' (A—NH$_2$=DX-8951)

Dextran T250 (20 g, EXTRASYNTHESE, average molecular weight: 250K) was dissolved in 0.1M acetic acid buffer (pH 5.5, 2000 ml) and added with an aqueous solution (2000 ml) of sodium periodate (66.0 g). After stirring at 4° C. for ten days with shielding the light, the mixture was added with ethylene glycol (14.0 ml) and stirred overnight. The reaction mixture was adjusted to pH 7.5 with 8M aqueous sodium hydroxide under ice-cooling. Sodium borohydride (28 g) was added and dissolved, and then the mixture was stirred overnight at room temperature. The reaction mixture was ice-cooled, adjusted to pH 5.5 with acetic acid and stirred at 4° C. for one hour, and then, adjusted to pH 7.5 with 8M aqueous sodium hydroxide under ice-cooling. The low molecular weight fraction was removed from the resulting aqueous solution by ultrafiltration using a Biomax-30 membrane to obtain Retained solution 1 that did not pass through the membrane. Separately, Dextran T250 (50 g, EXTRASYNTHESE, average molecular weight: 250K) was dissolved in 0.1M acetate buffer (pH 5.5, 5000 ml) and added with an aqueous solution (5000 ml) of sodium periodate (165 g). After stirring at 4° C. for ten days with shielding the light, the mixture was added with ethylene glycol (35.0 ml) and stirred overnight. The reaction mixture was adjusted to pH 7.5 with 8M aqueous sodium hydroxide under ice-cooling. Sodium borohydride (70 g) was added and dissolved, and then the mixture was stirred overnight at room temperature. The reaction mixture was ice-cooled, adjusted to pH 5.5 with acetic acid and stirred at 4° C. for one hour, and then, adjusted to pH 7.5 with 8M aqueous sodium hydroxide under ice-cooling. The low molecular weight fraction was removed from the resulting aqueous solution by ultrafiltration using a Biomax-30 membrane to obtain Retained solution 2 that did not pass through the membrane. Retained solutions 1 and 2 were combined, subjected to ultrafiltration using a Bliomax-30 membrane to remove the low molecular weight fraction from the fraction, that had passed through Biomax-50 membrane, and lyophilized to obtain dextran polyalcohol (25.7 g). The molecular weight of this substance was 47K (gel filtration, pullulan standard).

This dextran polyalcohol (5 g) was added to an aqueous solution obtained by dissolving sodium hydroxide (35 g) in water (150 ml) and dissolved at room temperature. To this solution, monochloroacetic acid (50 g) was added under ice-cooling and dissolved, and then the mixture was allowed to react at room temperature for 18 hours. This reaction mixture was adjusted to pH 8 with acetic acid and desalted by ultrafiltration using a Biomax-50 membrane. The remaining solution that had not passed through the membrane was lyophilized to obtain sodium salt of carboxymethyldextran polyalcohol (7.2 g). The molecular weight of this substance was 127K (gel filtration, pullulan standard) and the degree of carboxymethylation was 0.8. This sodium salt of carboxymethyldextran polyalcohol (2.2 g) was dissolved in water, applied to a Bio-Rad AG 50W-X2 (200–400 mesh, H$^+$ form) column (diameter: 44 mm, length: 210 mm) and eluted with water. This effluent was added with triethylamine (4 ml) and then lyophilized to give triethylammonium salt of carboxymethyldextran polyalcohol (2.69 g).

Figure 10:
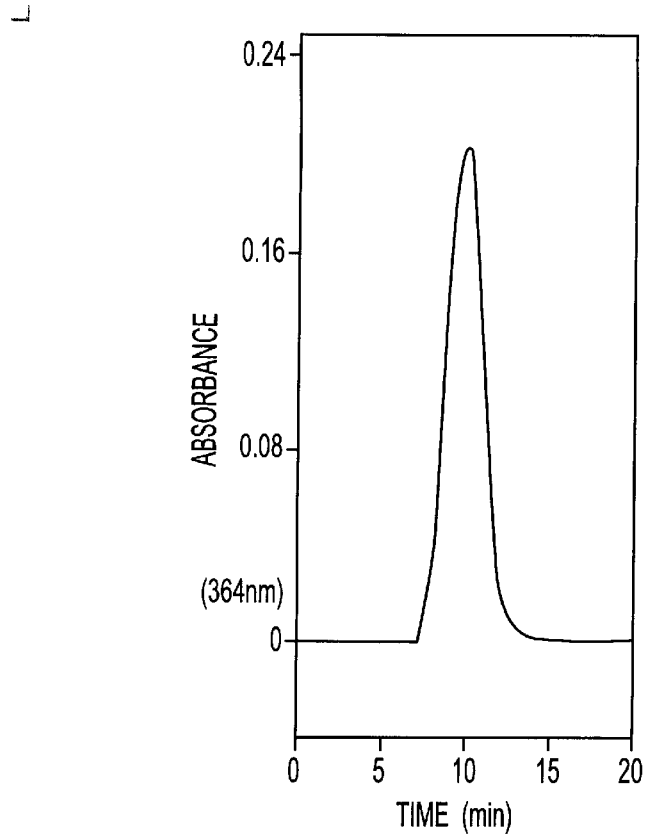
FIG. 10 shows the GPC chart of the drug complex of Example 29 prepared by the method of the present invention.
Figure 11:
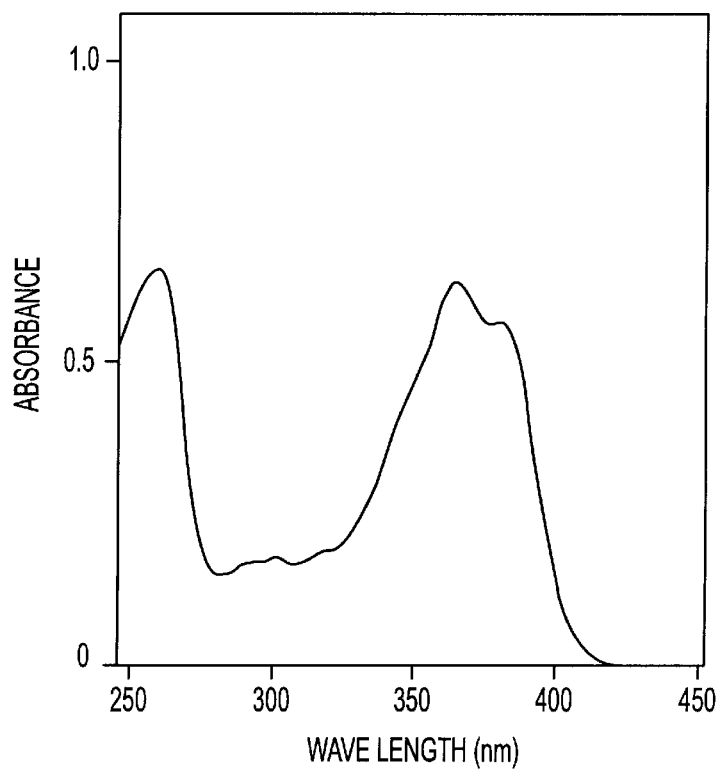
FIG. 11 shows the ultraviolet absorption spectrum of the drug complex of Example 29 prepared by the method of the present invention.

This triethylammonium salt of carboxymethyldextran polyalcohol (2.67 g) was dissolved in N,N-dimethylformamide (200 ml). To this solution, a solution obtained by dissolving the trifluoroacetic acid salt of 3'-N-(Gly-Gly-Gly-Phe)-NH—A, which had been obtained by removing the Boc group according to the method similar to that of Example 16 from 3'-N-(Boc-Gly-Gly-Gly-Phe)-NH—A (A—NH.=DX-8951) (350 mg) prepared in a similar manner to that of Example 2, and triethylamine (0.116 ml) in N,N-dimethylformamide (10 ml), and a solution obtained by dissolving 1-ethoxycarbonyl-2-ethoxy-1,2-dihydroxyquinoline (2.67 g) in N,N-dimethylformamide (10 ml) were added successively, and the mixture was allowed to react at room temperature overnight with stirring. This reaction mixture was added with 3M aqueous sodium chloride (100 ml) and each of 8 ml portions of the mixture was added dropwise to each 30 ml of ethanol. To each mixture, 3M aqueous sodium chloride (1 ml) and diethyl ether (5 ml) were added, and the precipitates deposited were collected by centrifugation (3500 rpm, 8 minutes). The precipitates were washed with acetone and then dissolved in water, and added with 3M aqueous sodium chloride (10 ml), and then adjusted to pH 9 with 0.1M aqueous sodium hydroxide, and further treated at 37° C. for 1 hour. The treated solution was desalted by ultrafiltration using a Biomax-10 membrane. The remaining solution that had not passed through the membrane was filtered through a Millipore filter (0.22 μm) and then lyophilized to give the title compound (2.30 g). The result obtained by GPC analysis after dissolving this compound in 0.1M aqueous sodium chloride (column: TSK Gel PW-4000XL, Tosoh, solvent: 0.1 M NaCl, flow rate: 0.8 ml/min) and the ultraviolet absorption spectrum of the compound (0.1M Tris buffer solution, pH 9.0, 0.20 mg/ml) are shown in FIG. 10 and FIG. 11, respectively. The content of the drug compound residue in the compound was 5.8% (W/W) when determined based on the absorption at 362 nm in 0.1 M Tris buffer solution (pH 9.0).

Example 30
Synthesis of Triethylammonium Salt of Carboxymethyldextran Polyalcohol To a solution (2000 ml) of Dextran T10 (20 g, Pharmacia, average molecular weight: 10K) in 0.1M acetic acid buffer (pH 5.5) was added an aqueous solution (2000 ml) of sodium periodate (66.0 g). After stirring at 4° C. for ten days with shielding the light, the mixture was added with ethylene glycol (14.0 ml) and stirred overnight. The reaction mixture was adjusted to pH 7.5 with 8M aqueous sodium hydroxide under ice-cooling. Sodium borohydride (28 g) was added and dissolved, and the mixture was stirred overnight at room temperature. The reaction mixture was ice-cooled, adjusted to pH 5.5 with acetic acid and stirred at 4° C. for one hour, and then, adjusted to pH 7.5 with 8M aqueous sodium hydroxide under ice-cooling. The resulting aqueous solution was subjected to ultrafiltration using a Biomax-5 membrane (Millipore) to remove the low molecular weight fraction, and the remaining solution that had not passed the membrane was passed through a Biomax-30 membrane. The resulting filtrate was lyophilized to obtain dextran polyalcohol (8.0 g). The molecular weight of this substance was 13K (gel filtration, pullulan standard).

This dextran polyalcohol (3.7 g) was added to an aqueous solution obtained by dissolving sodium hydroxide (25.9 g) in water (111 ml) and dissolved at room temperature. To this solution, monochloroacetic acid (37 g) was added under ice-cooling and dissolved, and then the mixture was allowed to react at room temperature for 20 hours. This reaction mixture was adjusted to pH 8 with acetic acid and desalted by ultrafiltration using a Biomax-5 membrane. The remaining solution that had not passed through the membrane was lyophilized to give sodium salt of carboxymethyldextran polyalcohol (6.2 g). The molecular weight of this substance was 37K (gel filtration, pullulan standard) and the degree of carboxymethylation was 0.9.

This sodium salt of carboxymethyldextran polyalcohol (6.0 g) was dissolved in water, applied to a Bio-Rad AG50W-X2 (200–400 mesh, $H^+$ form) column, and then eluted with water. This effluent was added with triethylamine (9.3 ml) and then lyophilized to obtain the title compound (7.2 g).

Example 31
Synthesis of Triethylammonium Salt of Carboxymethyldextran Polyalcohol The dextran polyalcohol (3.9 g) obtained in Example 30 was added to an aqueous solution obtained by dissolving sodium hydroxide (16.3 g) in water (117 ml) and dissolved at room temperature. To this solution, monochloroacetic acid (23.4 g) was added under ice-cooling and dissolved, and then the mixture was allowed to react at room temperature for 18 hours. This reaction mixture was adjusted to pH 8 with acetic acid and desalted by ultrafiltration using a Biomax-5 membrane. The remaining solution that had not passed through the membrane was lyophilized to obtain sodium salt of carboxymethyldextran polyalcohol (5.0 g). The molecular weight of this substance was 28K (gel filtration, pullulan standard) and the degree of carboxymethylation was 0.5. This sodium salt of carboxymethyldextran polyalcohol (4.8 g) was converted into the triethylammonium salt in a similar manner to that of Example 30 to obtain the title compound (5.6 g).

Example 32
Synthesis of Triethylammonium Salt of Carboxymethyldextran Polyalcohol An aqueous solution (2000 ml) of sodium periodate (66.0 g) was added to a solution (2000 ml) of Dextran 4 (20 g, Funakoshi, average molecular weight: 4K-6K) in 0.1M acetic acid buffer (pH 5.5). After stirring at 4° C. for ten days with shielding the light, the mixture was added with ethylene glycol (14.0 ml) and stirred overnight. The reaction mixture was adjusted to pH 7.5 with 8M aqueous sodium hydroxide under ice-cooling. Sodium borohydride (28 g) was added and dissolved, and the mixture was stirred overnight at room temperature. The reaction mixture was ice-cooled, adjusted to pH 5.5 with acetic acid and stirred at 4° C. for one hour, and then, adjusted to pH 7.5 with 8M aqueous sodium hydroxide under ice-cooling. The resulting aqueous solution was subjected to ultrafiltration using a Biomax-3 membrane (Millipore) to remove the low molecular weight fraction. The filtrate obtained was lyophilized to give dextran polyalcohol (6.0 g). The molecular weight of this substance was 9K (gel filtration, pullulan standard).This dextran polyalcohol (2.7 g) was added to an aqueous solution obtained by dissolving sodium hydroxide (18.9 g) in water (81 ml) and dissolved at room temperature. To this solution, monochloroacetic acid (27 g) was added under ice-cooling and dissolved, and then the mixture was allowed to react at room temperature for 20 hours. This reaction mixture was adjusted to pH 8 with acetic acid and desalted by ultrafiltration using a Biomax-5 membrane. The remaining solution that had not passed through the membrane was lyophilized to obtain sodium salt of carboxymethyldextran polyalcohol (4.2 g). The molecular weight of this substance was 20K (gel filtration, pullulan standard), and the degree of carboxymethylation was 0.9.

This sodium salt of carboxymethyldextran polyalcohol (4.0 g) was converted into the triethylammonium salt in a similar manner to that of Example 30 to obtain the title compound (4.8 g).

Example 33
Synthesis of Triethylammonium Salt of Carboxymethyldextran Polyalcohol The dextran polyalcohol (2.7 g) obtained in Example 32 was added to an aqueous solution obtained by dissolving sodium hydroxide (11.3 g) in water (81 ml) and dissolved at room temperature. To this solution, monochloroacetic acid (16.2 g) was added under ice-cooling and dissolved, and then the mixture was allowed to react at room temperature for 18 hours. This reaction mixture was adjusted to pH 8 with acetic acid and desalted by ultrafiltration using a Biomax-5 membrane. The remaining solution that had not passed through the membrane was lyophilized to obtain sodium salt of carboxymethyldextran polyalcohol (2.7 g). The molecular weight of this substance was 16K (gel filtration, pullulan standard) and the degree of carboxymethylation was 0.5. This sodium salt of carboxymethyldextran polyalcohol (2.7 g) was converted into the triethylammonium salt in a similar manner to that of Example 30 to obtain the title compound (3.1 g).

Example 34
Synthesis of Carboxymethyldextran Polyalcohol-Gly-Gly-Phe-Gly-NH—A' (A—$NH_2$=DX-8951)

Figure 12:
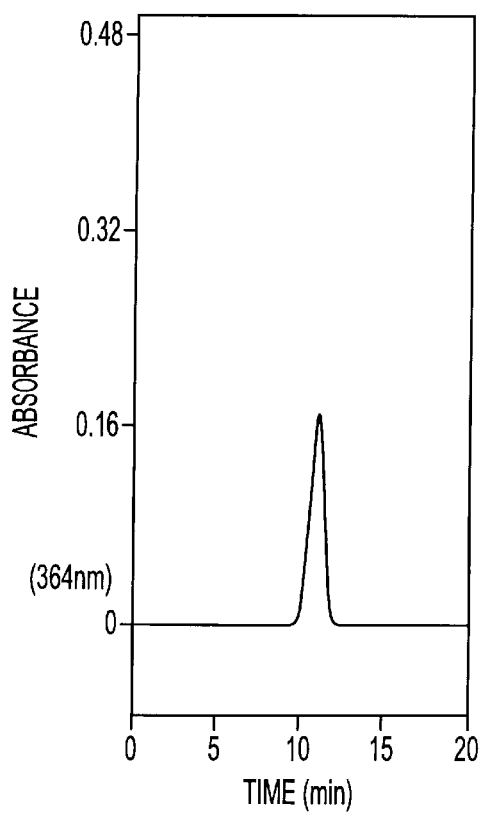
FIG. 12 shows the GPC chart of the drug complex of Example 34 prepared by the method of the present invention.
Figure 13:
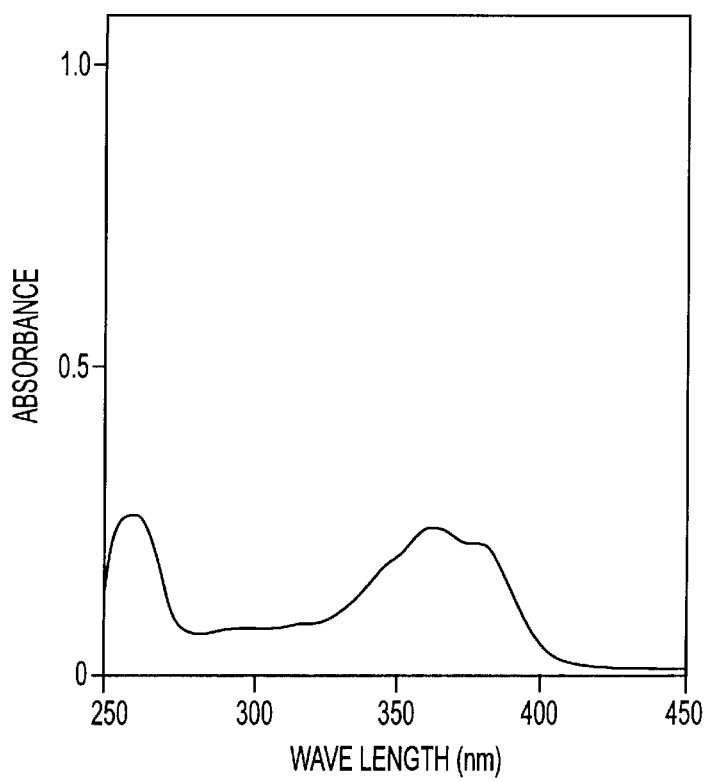
FIG. 13 shows the ultraviolet absorption spectrum of the drug complex of Example 34 prepared by the method of the present invention.

The triethylammonium salt of carboxymethyldextran polyalcohol obtained in Example 30 (1.5 g) was dissolved in N,N-dimethylformamide (90 ml). To this solution, a solution of triethylamine (0.07 ml) and trifluoroacetic acid salt of 3'-N-(Gly-Gly-Phe-Gly)-NH—A (A—$NH_2$=DX-8951) (210 mg) in N,N-dimethylformamide (40 ml), and 1-ethoxycarbonyl-2-ethoxy-1,2-dihydroxyquinoline (1.5 g) were added successively, and the mixture was allowed to react at room temperature overnight with stirring. Each of 5 ml portions of this reaction mixture was added dropwise to each 10 ml of ethanol. Each was added with 3M aqueous sodium chloride (2.5 ml) and diethyl ether (20 ml), and then the precipitates deposited were collected by centrifugation (3500 rpm, 8 minutes). The precipitates were dissolved in 0.5M aqueous sodium chloride and adjusted to pH 9 with 0.1M aqueous sodium hydroxide under ice-cooling. The resulting aqueous solution was desalted by ultrafiltration using a Biomax-3 membrane. The remaining solution that had not passed through the membrane was filtered through a Millipore filter (0.22 $\mu$m) and then lyophilized to obtain the title compound (1.3 g). The result obtained by GPC analysis after dissolving this compound in 0.1M aqueous sodium chloride (column: TSK Gel PW-4000XL, Tosoh, solvent: 0.1M NaCl, flow rate: 0.8 ml/min) and the ultraviolet absorption spectrum of the compound (0.1M Tris buffer solution, pH 9.0, 65 μg/ml) are shown in FIG. 12 and FIG. 13, respectively. The content of the drug compound residue in the compound was 6.4% (W/W) when determined based on the absorption at 362 nm in 0.1M Tris buffer solution (pH 9.0).

Example 35

Synthesis of Carboxymethyldextran Polyalcohol-Gly-Gly-Phe-Gly-NH—A' (A—NH$_2$=-DX-8951)

The triethylammonium salt of carboxymethyldextran polyalcohol obtained in Example 31(1.2 g) was dissolved in N,N-dimethylformamide (90 ml). To this solution, a solution of triethylamine (0.056 ml) and trifluoroacetic acid salt of 3'-N-(Gly-Gly-Phe-Gly)-NH—A (A—NH$_2$=DX-8951) (168 mg) in N,N-dimethylformamide (30 ml), and 1-ethoxycarbonyl-2-ethoxy-1,2-dihydroxyquinoline (1.2 g) were added successively, and the mixture was allowed to react at room temperature overnight with stirring. Each of 5 ml portions of this reaction mixture was added dropwise to each 10 ml of ethanol. Each was added with 3M aqueous sodium chloride (2.5 ml) and diethyl ether (20 ml), and the deposited precipitates were collected by centrifugation (3500 rpm, 8 minutes). The precipitates were dissolved in 0.5M aqueous sodium chloride and adjusted to pH 9 with 0.1M aqueous sodium hydroxide under ice-cooling. The resulting aqueous solution was desalted by ultrafiltration using a Biomax-3 membrane. The remaining solution that had not passed through the membrane was filtered through a Millipore filter (0.22 μm) and then lyophilized to obtain the title compound (1.0 g). The content of the drug compound residue in this compound was 4.8% (W/W) when determined based on the absorption at 362 nm in 0.1 M Tris buffer solution (pH 9.0).

Example 36

Synthesis of Carboxymethyldextran Polyalcohol-Gly-Gly-Phe-Gly-NH—A' (A—NH$_2$=DX-8951)

The triethylammonium salt of carboxymethyldextran polyalcohol obtained in Example 32 (1.2 g) was dissolved in N,N-dimethylformamide (90 ml). To this solution, a solution of triethylamine (0.056 ml) and trifluoroacetic acid salt of 3'-N-(Gly-Gly-Phe-Gly)-NH—A (A—NH$_2$=DX-8951) (168 mg) in N,N-dimethylformamide (30 ml), and 1-ethoxycarbonyl-2-ethoxy-1,2-dihydroxyquinoline (1.2 g) were added successively, and the mixture was allowed to react at room temperature overnight with stirring. Each of 5 ml portions of this reaction mixture was added dropwise to each 10 ml of ethanol. Each was added with 3M aqueous sodium chloride (2.5 ml) and diethyl ether (20 ml), and the deposited precipitates were collected by centrifugation (3500 rpm, 8 minutes). The precipitates were dissolved in 0.5M aqueous sodium chloride and adjusted to pH 9 with 0.1M aqueous sodium hydroxide under ice-cooling. The resulting aqueous solution was desalted by ultrafiltration using a Biomax-3 membrane. The remaining solution that had not passed through the membrane was filtered through a Millipore filter (0.22 μm) and then lyophilized to obtain the title compound (1.0 g). The content of the drug compound residue in this compound was 5.9% (W/W) when determined based on the absorption at 362 nm in 0.1 M Tris buffer solution (pH 9.0).

Example 37

Synthesis of Carboxymethyldextran Polyalcohol-Gly-Gly-Phe-Gly-NH—A' (A—NH$_2$=DX-8951)

The triethylammonium salt of carboxymethyldextran polyalcohol obtained in Example 33 (1.5 g) was dissolved in N,N-dimethylformamide (90 ml). To this solution, a solution of triethylamine (0.07 ml) and trifluoroacetic acid salt of 3'-N-(Gly-Gly-Phe-Gly)-NH—A (A—NH$_2$=DX-8951) (210 mg) in N,N-dimethylformamide (40 ml), and 1-ethoxycarbonyl-2-ethoxy-1,2-dihydroxyquinoline (1.5 g) were added successively, and the mixture was allowed to react at room temperature overnight with stirring. Each of 5 ml portions of this reaction mixture was added dropwise to each 10 ml of ethanol. Each was added with 3M aqueous sodium chloride (2.5 ml) and diethyl ether (20 ml), and the deposited precipitates were collected by centrifugation (3500 rpm, 8 minutes). The precipitates were dissolved in 0.5M aqueous sodium chloride and adjusted to pH 9 with 0.1M aqueous sodium hydroxide under ice-cooling. The resulting aqueous solution was desalted by ultrafiltration using a Biomax-3 membrane. The remaining solution that had not passed through the membrane was filtered through a Millipore filter (0.22 μm) and then lyophilized to obtain the title compound (1.3 g). The content of the drug compound residue in this compound was 4.6% (W/W) when determined based on the absorption at 362 nm in 0.1 M Tris buffer solution (pH 9.0).

Example 38

Synthesis of Boc-Gly-Gly-Phe-Gly-NH—A (A—NH$_2$=DW-8286)

Boc-Gly-Gly-Phe-Gly (42 mg) and N-hydroxysuccinimide (12 mg) were dissolved in N,N-dimethylformamide (2 ml), and cooled to 4° C., and then added with N,N'-dicyclohexylcarbodiimide (22 mg). To this solution, a solution of N,N-dimethylformamide (6 ml), in which hydrochloride of the compound represented by the following formula:

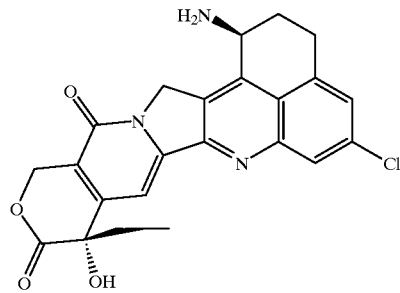

[(1s,9s)-1-amino-5-chloro-9-ethyl-2,3-dihydro-9-hydroxy-1H, 12H-benzo[de]pyrano-[3', 4':6,7]indolizino[1,2-b]quinoline-10,13(9H,5SH]-dione: DW-8286] (50 mg and triethylamine (0.01 ml) were dissolved, was added and the mixture was allowed to react with stirring and shielding the light at room temperature for 16 hours. This reaction mixture was evaporated to dryness under reduced pressure, and the residue was purified by silica gel column chromatography (eluent: dichloromethane:methanol=10:1 solution containing 0.5% acetic acid) to obtain the title compound (27 mg).

$^1$H-NMR (CDCl$_3$) δ : 8.10–8.20 (br, 1H), 7.95–8.05 (br, 1H), 7.70–7.80 (br, 2H), 7.50–7.60 (br, 1H), 7.40–7.50 (br, 1H1), 7.10–7.25 (m, 5H), 7.05–7.15 (br, 1H), 5.85–5.95(br, 1H), 5.50–5.60 (br, 1H), 5.40–5.50 (m, 1H), 5.25–5.3 5 (m, 1H), 5.05–5.15 (m, 1H), 4.90–5.00 (m, 1H), 4.70–4.80 (br, 1H), 4.10–4.25 (br, 2H), 3.60–3.90 (m, 4H), 3.10–3.40 (m,

3H), 2.95–3.05 (br, 1H), 2.15–2.30 (br, 1H), 1.75–1.90 (br, 2H), 1.39 (s, 9H), 0.80–1.00 (m, 3H).

Example 39
Synthesis of Carboxymethyldextran Polalcohol-Gly-Gly-Phe-Gly-NH—A' (A—NH$_2$=DW-8286)

Figure 14:
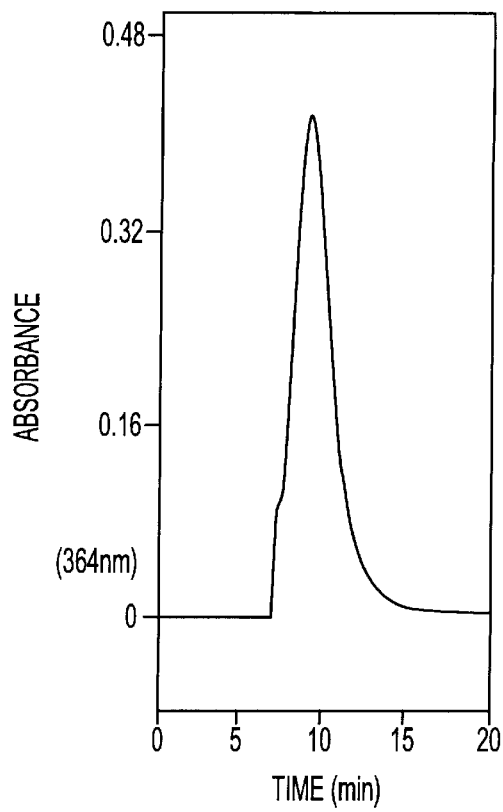
FIG. 14 shows the GPC chart of the drug complex of Example 39 prepared by the method of the present invention.
Figure 15:
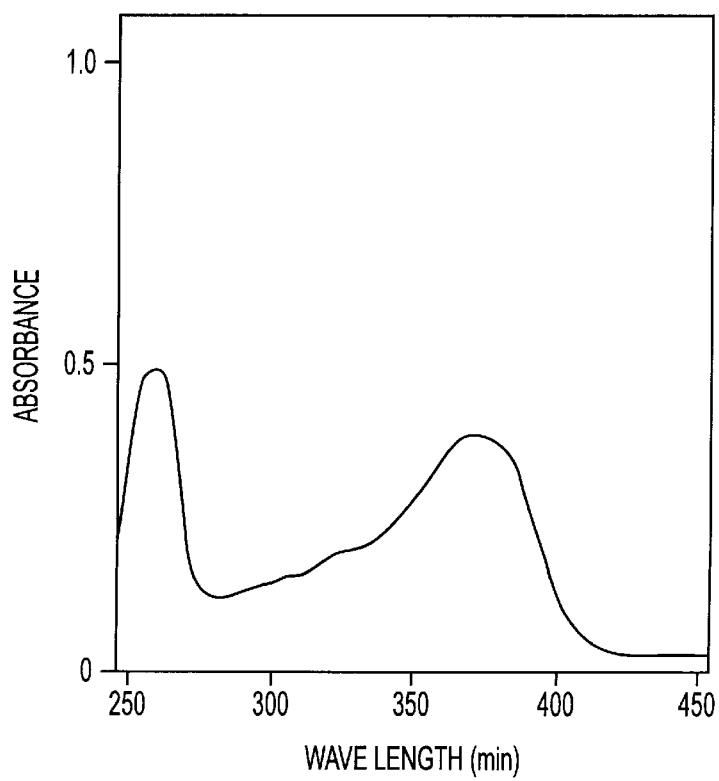
FIG. 15 shows the ultraviolet absorption spectrum of the drug complex of Example 39 prepared by the method of the present invention.

The triethylammonium salt of carboxymethyldextran polyalcohol (175 mg) obtained in Example 24 was dissolved in N,N-dimethylformamide (20 Ml). To this solution, a solution of trifluoroacetic acid salt of 3'-N-(Gly-Gly-Phe-Gly)-NH—A (A—NH$_2$=DW-8286) (29 mg), which had been obtained from 3'-N-(Boc-Gly-Gly-Phe-Gly)-NH—A (27 mg) prepared in Example 38 by removing the Boc group in a similar manner to that of Example 4, and triethylamine (9 μl) in N,N-dimethylformamide (5 ml), and 1-ethoxycarbonyl-2-ethoxy-1,2-dihydroxyquinoline (175 mg) were added successively, and the mixture was allowed to react at room temperature overnight with stirring. Each of 5 ml portions of this reaction mixture was added dropwise to each 10 ml of ethanol. The mixture was added with 3M aqueous sodium chloride (2.5 ml) and diethyl ether (20 ml), and the deposited precipitates were collected by centrifugation (3500 rpm, 8 minutes). The precipitates were dissolved in 0.5M aqueous sodium chloride and adjusted to pH 9 with 0.1M aqueous sodium hydroxide under ice-cooling. The resulting aqueous solution was desalted by ultrafiltration using a Biomax-30 membrane. The remaining solution that had not passed through the membrane was filtered through a Millipore filter (0.22 μm) and then lyophilized to obtain the title compound (135 mg). The result obtained by GPC analysis after dissolving this compound in 0.1M aqueous sodium chloride (column: TSK Gel PW-4000XL, Tosoh, solvent: 0.1 M NaCl, flow rate: 0.8 ml/min) and the ultraviolet absorption spectrum of the compound (0.1M Tris buffer solution, pH 9.0, 99 μg/ml) are shown in FIG. 14 and FIG. 15, respectively. The content of the drug compound residue in the compound was 6.1% (W/W) when determined based on the absorption at 362 nm in 0.1 M Tris buffer solution (pH 9.0).

Example 40
Synthesis of 3'-N-(Boc-(Gly-Gly-Phe-Gly)-NH—A (A—NH$_2$=DW-8089)

Boc-Gly-Gly-Phe-Gly (163 mg) and N-hydroxysuccinimide (45 mg) were dissolved in N,N-dimethylformamide (10 ml), cooled to 4° C., and then added with N,N'-dicyclohexylcarbodiimide (79 mg). To this solution, a solution of N,N-dimethylformamide (30 ml), in which tosylate of the compound represented by the following formula:

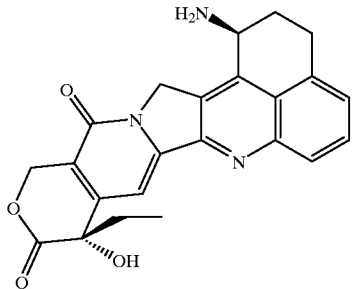

[(1s,9s)-1-amino-9-ethyl-2,3-dihydro-9-hydroxy-1H, 12H-benzo[de]pyrano[3',4':6,7]-indolizino[1,2-b]quinoline-10, 13(9H,15H)-dione: DW-8089] (170 mg) and triethylamine (0.054 ml) were dissolved, was added and the mixture was allowed to react with stirring at room temperature overnight under light-shielded conditions. This reaction mixture was evaporated to dryness under reduced pressure, and the residue was purified by silica gel column chromatography (eluent: dichloromethane:methanol=94:6 solution containing 0.5% acetic acid) to obtain the title compound (100 mg).

$^1$H-NMR (DMSO-d$_6$) δ : 8.51 (d, 1H, J=8.5 Hz), 8.41 (t, 1H, J=5.6 Hz), 8.29 (s, 1H), 8.17 (d, 1H, J=8.0 Hz), 8.03 (d, 1H, J=8.0 Hz), 7.90 (dd, 1H, J=4.8, 5.6 Hz), 7.79 (t, 1H, J=5.6 Hz), 7.53 (d, 1H, J=7.2 Hz), 7.36 (s, 1H), 7.13–7.25 (m, 5H), 6.94–6.95 (m, 1H), 5.60–5.63 (m, 1H), 5.36–5.47 (m, 2H), 5.21–5.30 (m, 2H), 4.42–4.47 (m, 1H), 3.63–3.96 (m, 3H), 3.51–3.59 (m, 3H), 3.31–3.40 (m, 1H), 3.09–3.21 (m, 1H), 3.02 (dd, 1H, J=4.8, 13.5 Hz), 2.76–2.81 (m, 1H), 2.13–2.17 (m, 2H), 1.85–1.90 (m, 2H), 1.37 (s, 9H), 0.89 (t, 3H, J=8.0 Hz); Mass (FAB); m/e 822 (M+1).

Example 41
Synthesis of Carboxymethyldextran Polyalcohol-Gly-Gly-Phe-Gly-NH—A' (A—NH$_2$=DW-8089)

Figure 16:
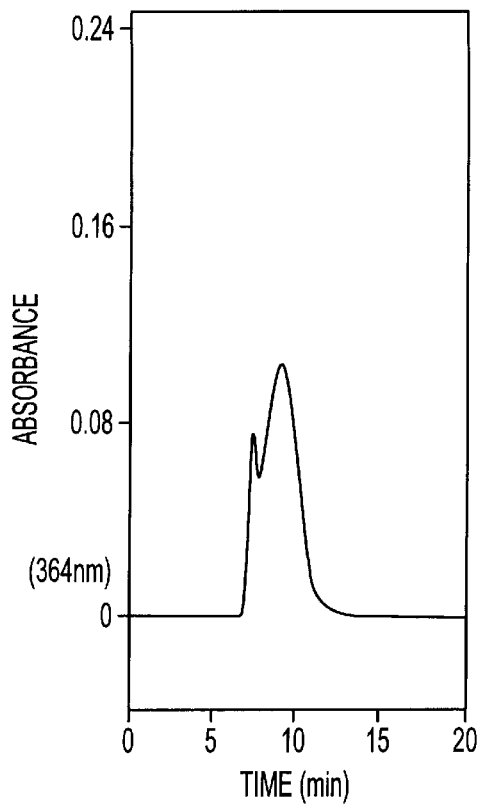
FIG. 16 shows the GPC chart of the drug complex of Example 41 prepared by the method of the present invention.
Figure 17:
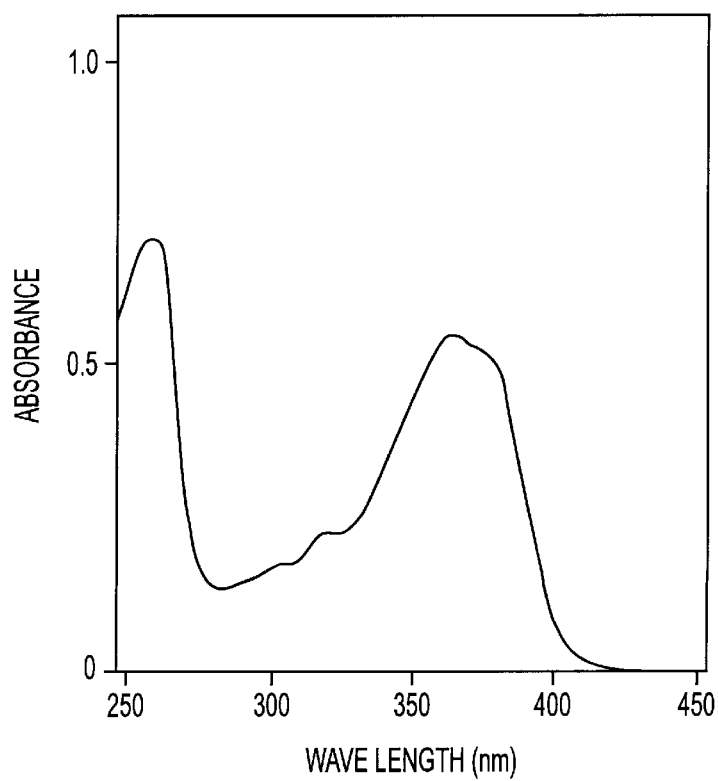
FIG. 17 shows the ultraviolet absorption spectrum of the drug complex of Example 41 prepared by the method of the present invention.

The triethylammonium salt of carboxymethyldextran polyalcohol (1.6 g) obtained in Example 24 was dissolved in N,N-dimethylformamide (60 ml). To this solution, a solution obtained by dissolving trifluoroacetic acid salt of 3'-N-(Gly-Gly-Phe-Gly)-NH—A (A—NH$_2$=DW-8089), which had been obtained from 3'-N-(Boc-Gly-Gly-Phe-Gly)-NH—A (200 mg) prepared in Example 40 by removing the Boc group in a similar manner to that of Example 4, and triethylamine (0.07 ml) in N,N-dimethylformamide (20 ml), and 1-ethoxycarbonyl-2-ethoxy-1,2-dihydroxyquinoline (1.6 g) were added successively, and the mixture was allowed to react at room temperature overnight with stirring. Each of 5 ml portions of this reaction mixture was added dropwise to each 10 ml of ethanol. Each was added with 3M aqueous sodium chloride (2.5 ml) and diethyl ether (25 ml), and the deposited precipitates were collected by centrifugation (2500 rpm, 8 minutes). The precipitates were washed with ethanol, then dissolved in water, added with 3M aqueous sodium chloride (20 ml), and adjusted to pH 9 with 0.1M aqueous sodium hydroxide. This solution was desalted by ultrafiltration using a Biomax-10 membrane. The remaining solution that had not passed through the membrane was filtered through a Millipore filter (0.22 μm) and then lyophilized to obtain the title compound (1.20 g). The result obtained by GPC analysis after dissolving the compound in 0.1M aqueous sodium chloride (column: TSK Gel PW-4000XL, Tosoh, solvent: 0.1 M NaCl, flow rate: 0.8 ml/min) and the ultraviolet absorption spectrum of the compound (0.1M Tris buffer solution, pH 9.0, 0.26 mg/ml) are shown in FIG. 16 and FIG. 17, respectively. The content of the drug compound residue in the compound was 5.0% (W/W) when determined based on the absorption at 362 nm in 0.1M Tris buffer solution (pH 9.0).

Example 42
Synthesis of Triethylammonium Salt of Carboxymethyldextran Polyalcohol Dextran T150 (20 g, Pharmacia, average molecular weight: 150K) was dissolved in 0.1M acetate buffer (pH 5.5, 2000 ml) and added with an aqueous solution (2000 ml) of sodium periodate (66.0 g). After stirring at 4° C. for ten days with shielding the light, the mixture was added with ethylene glycol (14.0 ml) and stirred overnight. The reaction mixture was adjusted to pH 7.5 with 8M aqueous sodium hydroxide under ice-cooling. Sodium borohydride (28 g) was added and dissolved, and then the mixture was stirred at room temperature overnight. The reaction mixture was ice-cooled, adjusted to pH 5.5 with acetic acid, and stirred at 4° C. for 1 hour. The pH of the mixture was adjusted to 7.5 with 8M aqueous sodium hydroxide under ice-cooling. The resulting aqueous solution was concentrated to 500 ml by ultrafiltration using a Biomax-5 membrane (Millipore) to obtain Solution 1. Separately, a series of proceduers described above was performed using Dextran T110 (20 g) to obtain Solution 2. Solution 1 and Solution 2 were combined, and the combined solution was adjusted to pH 3.0 and incubated at 40° C. for 4 hours, and then adjusted to pH 7 to obtain a solution containing the dextran polyalcohol with lowered molecular weight. The solution was passed through a Biomax-30 membrane and desalted by ultrafiltration using a Biomax-5 membrane, and then lyophilized to obtain dextran polyalcohol (4.6 g). The molecular weight of this substance was 17K (gel filtration, pullulan standard).

This dextran polyalcohol (2.5 g) was added to an aqueous solution obtained by dissolving sodium hydroxide (17.5 g) in water (75 ml) and dissolved at room temperature. To this solution, monochloroacetic acid (25 g) was added under ice-cooling and dissolved, and then the mixture was allowed to react at room temperature for 20 hours. This reaction mixture was adjusted to pH 9 with acetic acid and then desalted by ultrafiltration using a Biomax-5 membrane. The remaining solution that had not passed through the membrane was lyophilized to obtain sodium salt of carboxymethyldextran polyalcohol (4.0 g). The molecular weight of this substance was 45K (gel filtration, pullulan standard), and the degree of carboxymethylation was 0.9.

This sodium salt of carboxymethyldextran polyalcohol (3.7 g) was dissolved in water, applied to a Bio-Rad AG50W-X2 (200–400 mesh, $H^+$ form) column, and eluted with water. This eluent was added with triethylamine (5.8 ml) and then lyophilized to obtain the title compound (4.4 g).

Example 43
Synthesis of Carboxymethyldextran Polyalcohol-Gly-Gly-Gly-Phe-NH—A' (A—$NH_2$=)X-8951)

The triethylammonium salt of carboxymethyldextran polyalcohol obtained in Example 42 (4.4 g) was dissolved in N,N-dimethylformamide (300 ml). To this solution, a solution of triethylamine (0.19 ml) and trifluoroacetic acid salt of 3'-N-(Gly-Gly-Gly-Phe)-NH—A (A—$NH_2$=DX-8951) (580 mg) in N,N-dimethylformamide (45 ml) and 1-ethoxycarbonyl-2-ethoxy-1,2-dihydroxyquinoline (4.4 g) were added successively, and the mixture was allowed to react at room temperature overnight with stirring and shielding the light. This reaction mixture was adjusted to pH 10 with 1M aqueous sodium hydroxide, and then each of 5 ml portions of the mixture was added dropwise to each 25 ml of ethanol. The mixture was added with 3M aqueous sodium chloride (1 ml) and diethyl ether (5 ml), and the deposited precipitates were collected by centrifugation (3500 rpm, 8 minutes). The precipitates were dissolved in water and dialyzed against purified water using a dialysis membrane (Spectrapore 1, cut-off molecular weight; 6,000–8,000), and the inner dialyzate solution was filtered through a Millipore filter (0.22 µm) and then lyophilized to obtain the title compound (3.4 g). The content of the residue of the drug compound in this compound was 4.6% (W/W) when determined based on the absorption at 362 nm in 0.1M Tris buffer solution (pH 9.0).

Example 44
Synthesis of α-methylcarboxymethyldextran Polyalcohol-Gly-Gly-Gly-Phe-NH—A' (A—$NH_2$=DX-8951)

The dextran polyalcohol (2 g) obtained in Example 42 was added to an aqueous solution obtained by dissolving sodium hydroxide (14 g) in water (60 ml) and dissolved at room temperature. To this solution, α-bromopropionic acid (19 ml) was added under ice-cooling and dissolved, and then the mixture was allowed to react at room temperature for 18 hours. The reaction mixture was adjusted to pH 8 with acetic acid and desalted by ultrafiltration using a Biomax-50 membrane. The remaining solution that had not passed through the membrane was lyophilized to obtain sodium salt of α-methylcarboxymethyldextran polyalcohol (2.95 g). The molecular weight of this substance was 45K (gel filtration, pullulan standard). The degree of α-methylcarboxymethylation per saccharide residue was obtained according to the cases of carboxymethyldextran polyalcohol as follows. An aqueous solution of the sodium salt of α-methylcarboxymethyldextran polyalcohol was applied to a Bio-Rad AG 50W-X2 ($H^+$ form) column, and the effluent was lyophilized and used as a sample. This sample was dissolved in a prescribed excess amount of 0.1N aqueous solution of sodium hydroxide and titrated with 0.1N hydrochloric acid using phenolphthalein as an indicator. The degree of α-methylcarboxymethylation was obtained according to the equation: the degree of α-methylcarboxymethylation=13.4(a-b)/[s-7.2(a-b)] wherein "s" is the amount of sample used (mg), "a" is the prescribed excess amount of 0.1N aqueous solution of sodium hydroxide (ml), and "b" is the amount of 0.1N hydrochloric acid consumed for the titration (ml). As a result, the degree of α-methylcarboxymethylation was found to be 0.8.

This sodium salt of α-methylcarboxymethyldextran polyalcohol (2.2 g) was dissolved in water, applied to a Bio-Rad AG 50W-X2 (200–400 mesh, $H^+$ form) column (diameter: 44 mm, length: 210 mm), and then eluted with water. This effluent was added with triethylamine (4 ml) and then lyophilized to give triethylammonium salt of α-methylcarboxymethyldextran polyalcohol (2.69 g).

Figure 18:
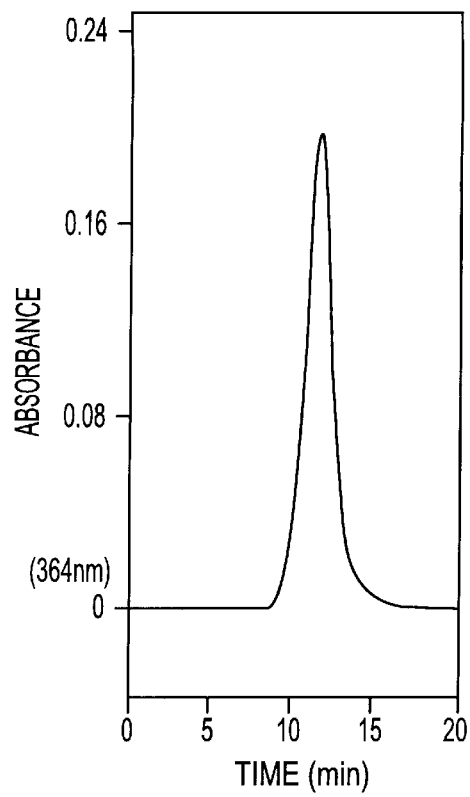
FIG. 18 shows the GPC chart of the drug complex of Example 44 prepared by the method of the present invention.
Figure 19:
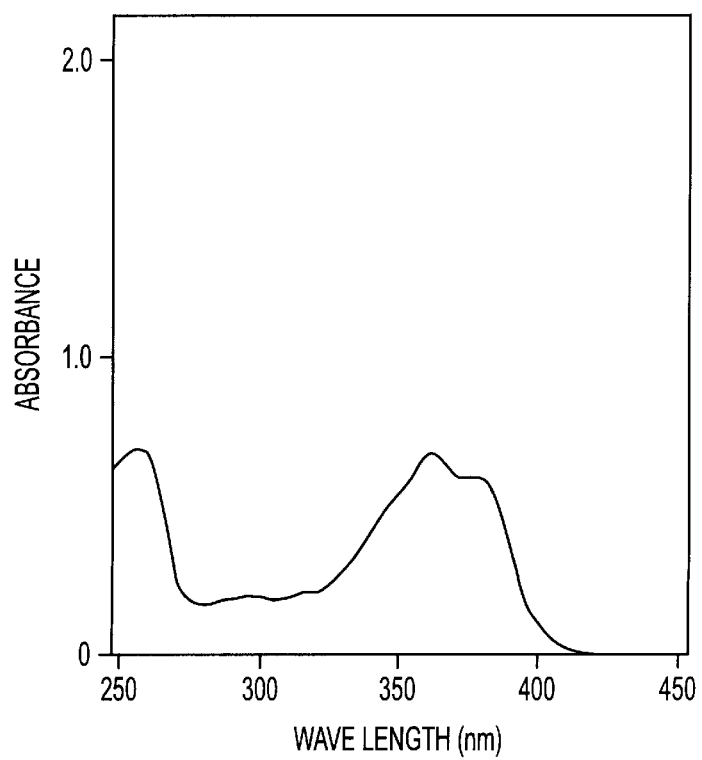
FIG. 19 shows the ultraviolet absorption spectrum of the drug complex of Example 44 prepared by the method of the present invention.

This triethylammonium salt of α-methylcarboxymethyldextran polyalcohol (2.68 g) was dissolved in N,N-dimethylformamide (60 ml). To this solution, a solution obtained by dissolving trifluoroacetic acid salt of 3'-N-(Gly-Gly-Gly-Phe)-NH—A (A—$NH_2$=DX-8951), which had been obtained in a similar manner to that of Example 16 by removing the Boc group from 3'-N-(Boc-Gly-Gly-Gly-Phe)-NH—A (350 mg) synthesized similarly to that of Example 2, and triethylamine (0.116 ml) in N,N-dimethylformamide (10 ml), and a solution obtained by dissolving 1-ethoxycarbonyl-2-ethoxy-1,2-dihydroxyquinoline (2.68 g) in N,N-dimethylformamide (10 ml) were added successively, and the mixture was allowed to react at room temperature overnight with stirring. This reaction mixture was added with 3M aqueous sodium chloride (40 ml), and each of 6 ml portions of the mixture was added dropwise to each 30 ml of ethanol. Each was added with 3M aqueous sodium chloride (1 ml) and diethyl ether (5 ml), and the precipitate deposited was collected by centrifugation (3500 rpm, 8 minutes). This precipitate was washed with acetone, then dissolved in water, added with 3M aqueous sodium chloride (10 ml), adjusted to pH 9 with 0.1M aqueous sodium hydroxide, and treated at 37° C. for 1 hour. This treated solution was desalted by ultrafiltration using a Biomax-10 membrane. The remaining solution that had not passed through the membrane was filtered through a Millipore filter (0.22 µm) and then lyophilized to obtain the title compound (2.15 g). The result obtained by GPC analysis after dissolving this compound in 0.1M aqueous sodium chloride (column: TSK Gel PW-4000XL, Tosoh, solvent: 0.1 M NaCl, flow rate: 0.8 ml/min) and the ultraviolet absorption spectrum of the compound (0.1M Tris buffer solution, pH 9.0, 0.21 mg/ml) are shown in FIG. 18 and FIG. 19, respectively. The content of the drug compound residue in the resulting product was 5.9% (W/W) when determined based on the absorption at 362 nm in 0.1 M Tris buffer solution (pH 9.0).

Example 45

Synthesis of 3'-N-(Gly-Phe-Gly)-NH—A (A—NH$_2$=DX-8951) Trifluoroacetic Acid Salt A mixture of p-toluenesulfonic acid salt of Phe-Gly-OBzl (3.06 g), Boc-Gly-OH (1.10 g), N-hydroxysuccinimide (941 mg), N-methylmorpholine (0.725 ml), and N,N-dimethylformamide (40 ml) was cooled to 4° C., and added with N,N'-dicyclohexylcarboduimide (1.56 g). The mixture was allowed to react overnight at room temperature with stirring, and then evaporated to dryness under reduced pressure. The residue was purified by silica gel column chromatography (eluent: dichloromethane:methanol=98:2 solution) to give Boc-Gly-Phe-Gly-OBzl (1.93 g).

$^1$H-NMR (DMSO-d$_6$) δ : 8.52 (dd, 1H, J=5.6, 6.4 Hz), 7.97 (d, 1H, J=8.8 Hz), 7.30–7.39 (m, 5H), 7.15–7.26 (m, 5H), 6.83 (t, 1H, J=5.6 Hz), 5.14 (s, 1H), 4.52–4.57 (m, 1H), 3.87–3.96 (m, 2H), 3.57 (dd, 1H, J=5.6, 16.7 Hz), 3.43 (dd, 1H, J=5.6, 16.7 Hz), 3.01 (dd, 1H, J=4.8, 14.3 Hz), 2.77 (dd, 1H, J=5.6, 14.3 Hz), 1.37 (s, 9H).

The resulting Boc-Gly-Phe-Gly-OBzl (1.78 g) was dissolved in ethyl acetate (60 ml) and subjected to catalytic reduction for 24 hours in the presence of 5%-Pd-C (1.8 g). The catalyst was removed by filtration and the filtrate was concentrated under reduced pressure to obtain Boc-Gly-Phe-Gly-OH (1.41 g).

$^1$H-NMR (DMSO-d$_6$) δ : 8.35 (t, 1H, J=5.6 Hz), 7.94 (d, 1H, J=8.8 Hz), 7.15–7.26 (m, 5H), 6.85 (dd, 1H, J=5.6, 6.4 Hz), 4.52–4.58 (m, 1H), 3.76 (d, 2H, J=5.6 Hz), 3.56 (dd, 1H, J=6.4, 16.7 Hz), 3.43 (dd, 1H, J=5.6, 16.7 Hz), 3.03 (dd, 1H, J=5.0, 13.5 Hz), 2.79 (dd, 1H, J=9.5, 13.5 Hz), 1.37 (s, 9H).

The Boc-Gly-Phe-Gly-OH (500 mg) obtained above and N-hydroxysuccinimide (161 mg) were dissolved in N,N-dimethylformamide (10 ml). To this solution, a N,N-dimethylformamide (50 ml) solution, in which methanesulfonate of DX-8951 (530 mg) and triethylamine (0.146 ml) were dissolved, was added. The mixture was cooled to 4° C., added with N,N'-dicyclohexylcarbodiimide (268 mg), and allowed to react overnight with stirring at room temperature under light-shielded conditions. This reaction mixture was evaporated to dryness under reduced pressure and the residue was purified by silica gel column chromatography (eluent: dichloromethane:methanol=96:4 solution) to obtain 3'-N-(Boc-Gly-Phe-Gly)-NH—A (A—NH$_2$=DX-8951) (100 mg).

$^1$H-NMR (DMSO-d$_6$) δ : 8.39 (d, 1H, J=8.0 Hz), 8.34 (t, 1H, J=5.6 Hz), 7.98 (d, 1H, J=7.2 Hz), 7.78 (d, 1H, J=10.3 Hz), 7.33 (s, 1H), 7.13–7.24 (m, 5H), 6.80 (dd, 1H, J=5.6, 6.4 Hz), 5.55–5.61 (m, 1H), 5.44 (d, 1H, J=16.0 Hz), 5.41 (d, 1H, J=16.0 Hz), 5.25 (s, 2H), 4.43–4.46 (m, 1H), 3.69–3.79 (m, 2H), 3.50 (dd, 1H, J=5.6, 16.7 Hz), 3.41 (dd, 1H, J=5.6, 16.7 Hz), 3.16–3.19 (m, 2H), 2.98 (dd, 1H, J=4.8, 14.3 Hz), 2.79 (dd, 1H, J=9.5, 14.3 Hz) 2.41 (s, 3H), 2.19–2.25 (m, 1H), 2.10–2.15 (m, 1H), 1.82–1.90 (m, 2H), 1.35 (s, 9H), 0.88 (t, 3H, J=8.0 Hz); Mass (FAB); m/e 797 (M+1).

The resulting 3'-N-(Boc-Gly-Phe-Gly)-NH—A (A—NH$_2$=DX-8951) (100 mg) was dissolved in trifluoroacetic acid (3 ml) and allowed to stand for one hour. The solvent was evaporated, and the residue was subjected to azeotropic distillations twice with methanol (30 ml) and twice with ethanol (30 ml), and then washed with ether to obtain the title compound (80 mg).

$^1$H-NMR (DMSO-d$_6$) δ : 8.52–8.62 (m, 1H), 7.94 (s, 3H), 7.79 (t, 1H, J=11.1 Hz), 7.34 (s, 1H), 7.15–7.27 (m, 5H), 6.52 (s, 1H), 5.57–5.61 (m, 1H), 5.36–5.46 (m, 2H), 4.66–4.70 (m, 1H), 3.69–3.81 (m, 2H), 3.61–3.68 (m, 1H), 3.40–3.47 (m, 1H), 3.15–3.23 (m, 1H), 3.01 (dd, 1H, J=4.0, 13.5 Hz), 2.77 (dd, 1H, J=9.5, 13.5 Hz), 2.12–2.23 (m, 2H), 1.81–1.91 (m, 2H), 0.89 (t, 3H, J=7.2 Hz); Mass (FAB); m/e 697 (M+1).

Example 46

Synthesis of 3'-N-(Phe-Gly)-NH—A (A—NH$_2$=DX-8951) Trifluoroacetic Acid Salt

Boc-Phe-Gly (771 mg) and N-hydroxysuccinimide (300 mg) were dissolved in N,N-dimethylformamide (10 ml). To this solution, a N,N-dimethylformamide (50 ml) solution, in which methanesulfonate of DX-8951 (1058 mg) and triethylamine (0.293 ml) were dissolved, was added. The mixture was cooled to 4° C., and then added with N,N'-dicyclohexylcarbodiimide (494 mg), and allowed to react with stirring at room temperature overnight under light-shielded conditions. This reaction mixture was evaporated to dryness under reduced pressure, and the residue was purified by silica gel column chromatography (eluent: dichloromethane:methanol=98:2 solution) to obtain 3'-N-(Boc-Phe-Gly)-NH—A (A—NH$_2$=DX-8951) (1.20 g).

$^1$H-NMR (DMSO-d$_6$) δ : 8.29 (d, 1H, J=8.0 Hz), 8.21 (t, 1H, J=4.8 Hz), 7.76 (d, 1H, J=10.3 Hz), 7.32 (s, 1H), 7.13–7.25 (m, 5H), 6.92 (d, 1H, J=7.2 Hz), 6.49 (s, 1H), 5.56–5.61 (m, 1H), 5.44 (d, 1H, J=15.9 Hz), 5.38 (d, 1H, J=15.9 Hz), 5.25 (s, 2H), 4.08–4.12 (m, 1H), 3.78 (d, 1H, J=4.8 Hz), 3.16–3.25 (m, 2H), 2.99 (dd, 1H, J=4.0, 13.5 Hz), 2.72 (dd, 1H, J=10.3, 13.5 Hz), 2.40 (s, 3H), 2.09–2.35 (m, 2H), 1.80–1.91 (m, 2H), 1.16 (s, 9H), 0.88 (t, 3H, J=8.0 Hz); Mass (FAB); m/e 741 (M+1).

The 3'-N-(Boc-Phe-Gly)-NH—A (170 mg) obtained above was dissolved in trifluoroacetic acid (4 ml) and allowed to stand for one hour. The solvent was evaporated, and the residue was subjected to azeotropic distillations twice with methanol (10 ml) and twice with ethanol (10 ml), and then washed with ether to obtain the title compound (100 mg).

$^1$H-NMR (DMSO-d$_6$) δ : 8.88 (t, 1H, J=4.8 Hz), 8.68 (d, 1H, J=8.7 Hz), 8.05–8.15 (m, 3H), 7.79 (d, 1H, J=11.1 Hz), 7.26–7.36 (m, 5H), 6.52 (d, 1H, J=7.2 Hz), 5.57–5.62 (m, 1H), 5.43 (d, 1H, J=15.9 Hz), 5.38 (d, 1H, J=15.9 Hz), 5.19–5.28 (m, 1H), 4.10–4.18 (m, 1H), 3.93 (dd, 1H, J=4.8, 16.7 Hz), 3.82 (dd, 1H, J=4.8, 16.7 Hz), 3.17–3.24 (m, 2H), 3.14 (dd, 1H, J=4.8, 13.5 Hz), 2.95 (dd, 1H, J=8.0, 13.5 Hz), 2.42 (s, 3H), 2.14–2.25 (m, 2H), 1.83–1.91 (m, 2H), 0.89 (t, 3H, J=8.0 Hz); Mass (FAB); m/e 640 (M+1).

Example 47

Synthesis of 3'-N-Gly-NH—A (A—NH$_2$=DX-8951) Trifluoroacetic Acid Salt

Methanesulfonate of DX-8951 (530 mg) and triethylamine (0.28 ml) were dissolved in N,N-dimethylformamide (10 ml), cooled to 4° C., and added with N-hydroxysuccinimide ester of Boc-Gly (327 mg). The mixture was allowed to react with stirring at room temperature overnight under light-shielded conditions. This reaction mixture was evaporated to dryness under reduced pressure, and then the residue was purified by silica gel column chromatography (eluent: dichloromethane:methanol=98:2 solution) to obtain 3'-N-(Boc-Gly)-NH—A (A—NH$_2$=DX-8951) (500 mg).

$^1$H-NMR (DMSO-d$_6$) δ : 8.38 (d, 1H, J=8.3 Hz), 7.77 (d, 1H, J=10.7 Hz), 7.31 (s, 1H), 6.89–6.91 (m, 1H), 6.49 (s, 1H), 5.55–5.59 (m, 1H), 5.45 (d, 1H, J=16.1 Hz), 5.38 (d,

1H, J=16.1 Hz), 5.27 (d, 1H, J=19.0 Hz), 5.18 (d, 1H, J=19.0 Hz), 3.50–3.62 (m, 2H), 3.15–3.19 (m, 2H), 2.41 (s, 3H), 2.18–2.24 (m, 1H), 2.08–2.12 (m, 1H), 1.81–1.91 (m, 2H), 1.31 (s, 9H), 0.87 (t, 3H, J=8.0 Hz); Mass (FAB); m/e 593 (M+1).

The 3'-N-(Boc-Gly)-NH—A (100 mg) obtained above was dissolved in trifluoroacetic acid (2 ml) and allowed to stand for one hour. The solvent was evaporated, and the residue was subjected to azeotropic distillations twice with methanol (10 ml) and twice with ethanol (10 ml), and then washed with ether to obtain the title compound (70 mg).

$^1$H-NMR (DMSO-$d_6$) δ : 8.88 (d, 1H, J=8.8 Hz), 8.08 (s, 3H), 7.81 (d, 1H, J=11.2 Hz), 7.34 (s, 1H), 6.52 (s, 1H), 5.63–5.67 (m, 1H), 5.45 (d, 1H, J=16.7 Hz), 5.40 (d, 1H, J=16.7 Hz), 5.36 (d, 1H, J=19.1 Hz), 5.25 (d, 1H, J=19.1 Hz), 3.56 (s, 2H), 3.11–3.19 (m, 2H), 2.43 (s, 3H), 2.23–2.28 (m, 1H), 2.11–2.19 (m, 1H), 1.81–1.91 (m, 2H), 0.88 (t, 3H, J=8.0 Hz); Mass (FAB); m/e 493 (M+1).

Example 48
Synthesis of Trimethylammonium Salt of Carboxymethyldextran Polyalcohol Dextran T500 (50 g, Pharmacia, molecular weight: 500K) was dissolved in 0.1M acetate buffer (pH 5.5, 5000 ml) and added with an aqueous solution (5000 ml) of sodium periodate (165.0 g). After stirring at 4° C. for ten days with shielding the light, the mixture was added with ethylene glycol (35.0 ml) and stirred overnight. The reaction mixture was adjusted to pH 7 with 8M aqueous sodium hydroxide. Sodium borohydride (70 g) was added and dissolved, and the mixture was stirred overnight. The reaction mixture was ice-cooled, adjusted to pH 5.5 with acetic acid and stirred at 4° C. for one hour, and then, adjusted to pH 7.5 with 8M aqueous sodium hydroxide. The resulting aqueous solution was desalted by ultrafiltration using a Biomax-50 membrane. The remaining solution that had not passed through the membrane was lyophilized to obtain dextran polyalcohol (20.2 g). The molecular weight of this substance was 159K (gel filtration, pullulan standard).

This dextran polyalcohol (7.5 g) was added to an aqueous solution obtained by dissolving sodium hydroxide (31.5 g) in water (225 ml) and dissolved at room temperature. To this solution, monochloroacetic acid (45 g) was added under ice-cooling and dissolved, and the mixture was allowed to react at room temperature overnight. This reaction mixture was adjusted to pH 8 with acetic acid and then desalted by ultrafiltration using a Biomax-50 membrane. The remaining solution that had not passed through the membrane was lyophilized to obtain sodium salt of carboxymethyldextran polyalcohol (8.5 g). The molecular weight of this substance was 274K (gel filtration, pullulan standard), and the degree of carboxymethylation was 0.4. This sodium salt of carboxymethyldextran polyalcohol (2.0 g) was dissolved in water, applied to a Bio-Rad AG 50W-X2 (200–400 mesh, H$^+$ form) column (diameter: 44 mm, length: 210 mm), and eluted with water. This effluent was added with triethylamine (4 ml) and then lyophilized to obtain the title compound (2.2 g).

Example 49
Synthesis of Carboxymethyldextran Polyalcohol-Gly-Phe-Gly-NH—A' (A—NH$_2$=DX-8951)

The triethylammonium salt of carboxymethyldextran polyalcohol obtained in Example 48 (200 mg) was dissolved in N,N-dimethylformamide (7 ml). To this solution, a solution of the trifluoroacetic acid salt of 3'-N-(Gly-Phe-Gly)-NH—A (A—NH$_2$=DX-8951) obtained in Example 45 (41 mg) in N,N-dimethylformamide (5 ml), triethylamine (0.014 ml), and 1-ethoxycarbonyl-2-ethoxy-1,2-dihydroxyquinoline (100 mg) were added successively, and the mixture was allowed to react at room temperature overnight with stirring. Each of 5 ml portions of this reaction mixture was added dropwise to each 10 ml of ethanol. The mixture was added with 3M aqueous sodium chloride (2.0 ml) and diethyl ether (25 ml), and the deposited precipitates were collected by centrifugation (3500 rpm, 8 minutes). The precipitates were dissolved in 0.5M aqueous sodium chloride and adjusted to pH 9 with 0.1M aqueous sodium hydroxide under ice-cooling. The resulting aqueous solution was desalted by ultrafiltration using a Biomax-50 membrane. The remaining solution that had not passed through the membrane was filtered through a Millipore filter (0.22 μm) and then lyophilized to obtain the title compound (190 mg). The content of the drug compound residue in this compound was 4.5% (W/W) when determined based on the absorption at 362 nm in 0.1M Tris buffer (pH 9.0).

Example 50
Synthesis of Carboxymethyldextran Polyalcohol-Phe-Gly-NH—A' (A—NH$_2$=DX-8951)

The sodium salt of carboxymethyldextran polyalcohol obtained in Example 24 (2.5 g) was dissolved in water, applied to a Bio-Rad AG 50W-X2 (200–400 mesh, Et$_3$N H$^+$ form) column, and eluted with water. This effluent was lyophilized to give triethylammonium salt of carboxymethyldextran polyalcohol (2.5 g).

This triethylammonium salt of carboxymethyldextran polyalcohol (200 mg) was dissolved in N,N-dimethylformamide (12 ml). To this solution, a solution of the trifluoroacetic acid salt of 3'-N-(Phe-Gly)-NH—A (A—NH$_2$=DX-8951) (42 mg) obtained in Example 46 and triethylamine (0.016 ml) in N,N-dimethylformamide (5 ml), and 1-ethoxycarbonyl-2-ethoxy-1,2-dihydroxyquinoline (200 mg) were added successively, and the mixture was allowed to react at room temperature overnight with stirring and shielding the light. This reaction mixture was added with water (300 ml) and subjected to ultrafiltration using a ultrafiltration membrane 10K (Filtron). The remaining solution that had not passed through the membrane was adjusted to pH 10 with 0.1N aqueous sodium hydroxide, and passed through a filtration membrane (0.16 μm, Filtron). The filtrate was desalted by ultrafiltration using a Biomax-50 membrane, and then filtered through a Millipore filter (0.22 μm) and lyophilized to obtain the title compound (180 mg). The content of the drug compound residue in this compound was 6.1% (W/W) when determined based on the absorption at 362 nm in 0.1 M Tris buffer solution (pH 9.0).

Example 51
Synthesis of Carboxymethyldextran Polyalcohol-Gly-NH—A' (A—NH$_2$=DX-8961)

The triethylammonium salt of carboxymethyldextran polyalcohol obtained in Example 48 (370 mg) was dissolved in N,N-dimethylformamide (10 ml). To this solution, a solution of the trifluoroacetic acid salt of 3'-N-Gly-NH—A (A—NH$_2$=DX-8951) obtained in Example 47 (57 mg) in N,N-dimethylformamide (3 ml), triethylamine (0.027 imnl), and 1-ethoxycarbonyl-2-ethoxy-1,2-dihydroxyquinoline (185 mg) were added successively, and then the mixture was allowed to react at room temperature overnight with stirring. Each of 5 ml portions of this reaction mixture was added dropwise to each 10 ml of ethanol. The mixture was added with 3M aqueous sodium chloride (2.0 ml) and diethyl ether (25 ml), and the deposited precipitates were collected by centrifugation (3500 rpm, 8 minutes). The precipitates were dissolved in 0.5M aqueous sodium chloride and adjusted to pH 9 with 0.1M aqueous sodium hydroxide under ice-cooling. The resulting aqueous solution was desalted by ultrafiltration using a Biomax-50 membrane. The remaining solution that had not passed through the membrane was filtered through a Millipore filter (0.22 μm) and then lyophilized to obtain the title compound (290 mg). The content of the drug compound residue in this compound was 0.5% (W/W) when determined based on the absorption at 362 nm in 0.1M Tris buffer (pH 9.0).

Example 52
Antitumor Activity of the Drug Complex of the Present Invention

Meth A tumor-bearing mice (6 mice per group) were prepared according to a similar manner to that of Example 11 and the antitumor activity of the drug complex of Example 15 was examined by single administration in a similar manner to that of Example 12. As a result, the drug complex of Example 15 exhibited remarkably enhanced antitumor activity and broader effective dose-range compared to the drug compound itself of Example 12.

| Test compound | Dose (mg/kg)[1] | Inhibition rate (%) |
|---|---|---|
| Compound of Example 15 | 10 | 100 |
| | 5 | 99 |
| | 2.5 | 95 |
| | 1.25 | 83 |

[1] Calculated based on the drug compound

Example 53
Antitumor Activity of the Drug Complex of the Present Invention

SC-6 tumor-bearing nude mice (5 mice per group) were prepared by subcutaneously transplanting a piece of SC-6 human gastric tumor block into the right inguinal regions of nude mice (13AI,B/c-nu/nu, male). On day 27 after the transplantation, the drug complex of Example 15 dissolved in distilled water for injection was given as a single intravenous administration and its antitumor activity was compared to that of the drug compound, per se. As a result, the drug complex of Example 15 exhibited higher antitumor activity compared to the drug compound, per se, whereas there was no death due to toxicity.

| Test compound | Dose (mg/kg) | Inhibition rate (%) | Numbers of died mice/mice used |
|---|---|---|---|
| Drug compound, per se | 60 | 98 | 2/5 |
| | 15 | 61 | 0/5 |
| Compound of Example 15 | 8[1] | 100 | 0/5 |
| | 2[1] | 71 | 0/5 |

[1] Calculated based on the drug compound

Example 54
Antitumor Activity of the Drug Complex of the Present Invention

Human lung cancer QG-90-bearing nude mice (5 mice per group) were prepared according to a similar manner to that of Example 53. On day 16 after the transplantaion, the drug complex of Example 15 dissolved in distilled water for injection was given as a single intravenous administration and its antitumor activity was compared to that of the drug compound, per se. As a result, the drug complex of Example 15 exhibited remarkably enhanced antitumor activity and broader effective dose-range compared to the drug compound, per se.

| Test compound | Dose (mg/kg) | Inhibition rate (%) | Numbers of died mice/mice used |
|---|---|---|---|
| Drug compound, per se | 50 | 65 | 0/5 |
| | 12.5 | 51 | 0/5 |
| Compound of Example 15 | 7[1] | 98 | 0/5 |
| | 1.75[1] | 97 | 0/5 |

[1] Calculated based on the drug compound

Example 55
Antitumor Activity of the Drug Complex of the Present Invention

Meth A tumor-bearing mice (6 mice per group) were prepared according to a similar manner to that of Example 1, and the antitumor activity of the drug complex of Example 41 was examined in the cases of single administration in a similar manner to that of Example 12, and its antitumor activity was compared to that of the drug compound, per se. As a result, the drug complex of Example 41 exhibited remarkably enhanced antitumor activity and broader effective dose-range compared to the drug compound, per se.

| Test compound | Dose (mg/kg) | Inhibition rate (%) |
|---|---|---|
| Drug compound, per se | 100 | 64 |
| | 50 | 56 |
| | 25 | 34 |
| Compound of Example 41 | 25[1] | 99 |
| | 12.5[1] | 95 |
| | 6.25[1] | 81 |
| | 3.125[1] | 61 |

[1] Calculated based on the drug compound

Example 56
Antitumor Activity of the Drug Complex of the Present Invention

Meth A tumor-bearing mice (6 mice per group) were prepared according to a similar manner to that of Example 11, and the antitumor activity was examined according to a similar method to that in Example 12 by single administration of the drug complexes of Examples 29, 43, and 44, respectively. As a result, all of the drug complexes exhibited high antitumor activity and broader effective dose-range.

| Test compound | Dose (mg/kg)[1] | Inhibition rate (%) |
|---|---|---|
| Compound of Example 29 | 30 | 99 |
| | 20 | 99 |
| | 10 | 89 |
| | 5 | 79 |
| Compound of Example 43 | 100 | 94 |
| | 80 | 92 |
| | 40 | 82 |
| | 20 | 75 |
| Compound of Example 44 | 100 | 96 |
| | 80 | 94 |
| | 40 | 97 |
| | 20 | 75 |

[1] Calculated based on the drug compound

Example 57
Pharmacokinetics of the Drug Complex of the Present Invention

Figure 20:
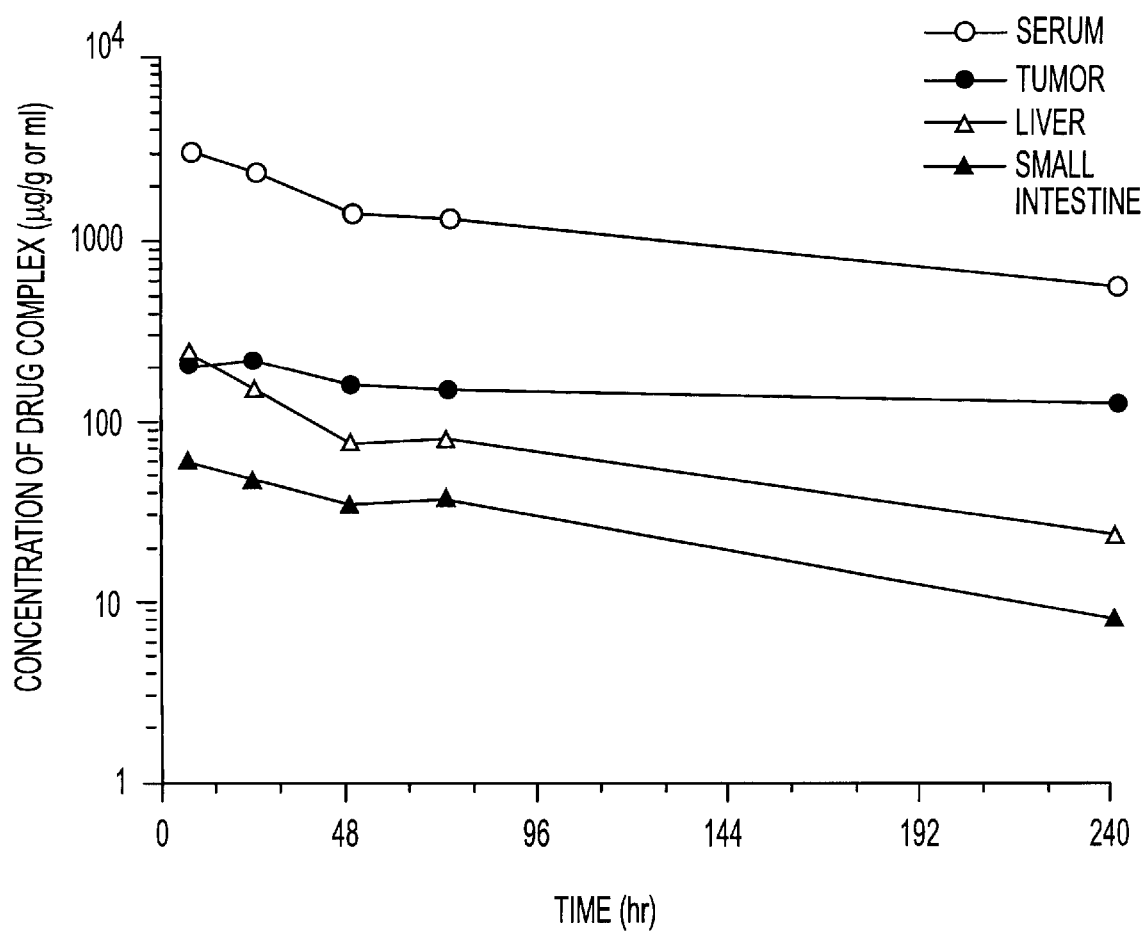
FIG. 20 shows the pharmacokinetics of the drug complex of Example 15 prepared by the method of the present invention. Each point in the figure represents an average value of three experiments.

Meth A tumor-bearing mice were prepared according to a similar manner to that of Example 11, the drug complex of Example 15 was given as single administration in a similar manner to that of Example 12 (10 mg/kg: calculated as the drug compound), and the change of the drug complex concentration in various tissues was determined. As a result, the drug complex of Example 15 was found to have extremely long retention of blood level, high distribution in tumor tissues, and high tumor selectivity against liver and small intestine. The results are shown in FIG. 20.

Industrial Applicability

The reaction between the polysaccharide derivative having carboxyl groups and the drug compound bound with the spacer or the like can be carried out in high yield, and when a drug compound having a lactone ring is subjected to the reaction, side reactions can be reduced, and therefore, the method of the present invention is quite useful as a process for preparing the drug complex.

What is claimed is:

1. A method for preparing a drug complex in which a polysaccharide derivative having carboxyl groups and a residue of a drug compound having a lactone ring are bound to each other with a spacer comprising an amino acid or peptide-bonded 2 to 8 amino acids or are bound to each other without the spacer, the method comprising reacting an organic amine salt of the polysaceharide derivative having carboxyl groups with the drug compound or with the spacer bound to the drug compound in a non-aqueous system.

2. A method for preparing a drug complex in which a polysaccharide derivative having carboxyl groups and a residue of a drug compound a are bound to each other with a spacer comprising an amino acid or peptide-bonded 2 to 8 amino acids or are bound to each other without the spacer, wherein the method comprises:
    converting an alkali metal salt of the polysaccharide derivative having carboxyl groups into an organic amine salt thereof, and
    reacting the organic amine salt of the polysaccharide derivative having carboxyl groups with the drug compound or with the spacer bound to the drug compound in a non-aqueous system.

3. The method of claim 1 wherein the polysaceharide derivative having carboxyl groups is carboxy($C_{1-4}$) alkyldextran polyalcohol.

4. The method of claim 3, wherein the carboxy($C_{1-4}$)alkyl dextran polyalcohol is obtained by treating dextran under conditions that enable substantially complete polyalcoholization.

5. The method of claim 3 wherein the carboxy($C_{1-4}$) alkyldextran polyalcohol is carboxymethyldextran polyalcohol.

6. The method according to claim 1, wherein the drug compound is an antineoplastic agent or an anti-inflammatory agent.

7. The method of claim 1 wherein the polysaccharide derivative having carboxyl groups is carboxymethyldextran polyalcohol having a molecular weight in the range of from 200,000 to 400,000.

8. The method of claim 1 wherein the polysacclaride derivative having carboxyl groups is selected from hyaluronic acid, pectic acid, alginic acid, chondroitin, heparin, pullulan, dextran, mannan, chitin, inulin, levan, xylan, araban, mannoglucan or chitosan.

9. The method of claim 1 wherein the polysaccharide derivative having carboxyl groups is selected from trimethylammonium salt of carboxymethyldextran polyalcohol or triethylammonium salt of carboxymethyldextran polyalcohol.

10. The method of claim 2 wherein the polysaccharide derivative having carboxyl groups is carboxy($C_{1-4}$) alkyldextran polyalcohol.

11. The method of claim 10, wherein the carboxy($C_{1-4}$) alkyl dextran polyalcohol is obtained by treating dextran under conditions that enable substantially complete polyalcoholization.

12. The method of claim 10 wherein the carboxy($C_{1-4}$) alkyldextran polyalcohol is carboxymethyldextran polyalcohol.

13. The method of claim 2, wherein the drug compound is an antineoplastic agent or an anti-inflammatory agent.

* * * * *

UNITED STATES PATENT AND TRADEMARK OFFICE
CERTIFICATE OF CORRECTION

PATENT NO. : 6,291,671 B1
DATED : September 18, 2001
INVENTOR(S) : K. Inoue et al.

It is certified that error appears in the above-identified patent and that said Letters Patent is hereby corrected as shown below:

<u>Column 43,</u>
Line 30, "polysaceharide" should be -- polysaccharide --.
Line 35, "a" (second occurrence) should be -- having a lactone ring --.

<u>Column 44,</u>
Line 3, "polysaceharide" should be -- polysaccharide --.
Line 21, "polysacclaride" should be -- polysaccharide --

Signed and Sealed this

Fifth Day of November, 2002

*Attest:*

JAMES E. ROGAN
*Attesting Officer*   *Director of the United States Patent and Trademark Office*